United States Patent
Mitamura et al.

(10) Patent No.: US 6,958,080 B2
(45) Date of Patent: Oct. 25, 2005

(54) COMPOSITIONS FOR DYEING KERATINOUS FIBER

(75) Inventors: Joji Mitamura, Tokyo (JP); Mutsumi Noguchi, Tokyo (JP); Takeshi Onuki, Tokyo (JP)

(73) Assignee: Lion Corporation, Tokyo (JP)

( * ) Notice: Subject to any disclaimer, the term of this patent is extended or adjusted under 35 U.S.C. 154(b) by 77 days.

(21) Appl. No.: 10/148,621

(22) PCT Filed: Dec. 1, 2000

(86) PCT No.: PCT/JP00/08525

§ 371 (c)(1),
(2), (4) Date: May 31, 2002

(87) PCT Pub. No.: WO01/39736

PCT Pub. Date: Jun. 7, 2001

(65) Prior Publication Data

US 2003/0106166 A1 Jun. 12, 2003

(30) Foreign Application Priority Data

Dec. 2, 1999 (JP) .............................. 11-343930

(51) Int. Cl.⁷ .............................. A61K 7/13; C09B 67/00
(52) U.S. Cl. ..................... 8/401; 8/406; 8/407; 8/408; 8/426
(58) Field of Search ........................... 8/401, 406, 407, 8/408, 426

(56) References Cited

U.S. PATENT DOCUMENTS

| 3,251,742 A | | 5/1966 | Soloway et al. | |
|---|---|---|---|---|
| 4,025,301 A | * | 5/1977 | Lang | 8/405 |
| 4,808,189 A | * | 2/1989 | Oishi et al. | 8/408 |
| 4,961,925 A | * | 10/1990 | Tsujino et al. | 424/70.2 |
| 5,480,460 A | * | 1/1996 | Muraoka | 8/416 |
| 5,667,531 A | * | 9/1997 | Yaver et al. | 8/401 |
| 5,849,041 A | * | 12/1998 | Kunz et al. | 8/408 |
| 5,948,121 A | * | 9/1999 | Aaslyng et al. | 8/401 |
| 6,106,579 A | | 8/2000 | Kunz et al. | |
| 2003/0074743 A1 | * | 4/2003 | Noguchi et al. | 8/401 |

FOREIGN PATENT DOCUMENTS

| EP | 09 716 846 A1 | 6/1996 |
|---|---|---|
| EP | 0 943 316 A2 | 9/1999 |
| EP | 1 043 012 A2 | 10/2000 |
| EP | 1 142 563 A1 | 10/2001 |
| JP | 47-10400 | 5/1972 |
| JP | 53-32132 A | 3/1978 |
| JP | 63-246313 A | 10/1988 |
| JP | 6-172145 A | 6/1994 |
| JP | 8-175935 A | 7/1996 |
| JP | 8-217652 A | 8/1996 |
| JP | 11-60454 A | 3/1999 |
| JP | 2000-503042 A | 3/2000 |
| JP | 2000-336201 A | 12/2000 |
| WO | 97/19998 A1 | 6/1997 |
| WO | 00/57848 A1 | 10/2000 |

OTHER PUBLICATIONS

"Science of Wave", Japan Permanent Waving Lotion Industry Association, issued by Shinbiyo Shuppan Co,. Ltd., 1994 (with partial translation).

* cited by examiner

*Primary Examiner*—Margaret Einsmann
(74) *Attorney, Agent, or Firm*—Birch, Stewart, Kolasch & Birch, LLP

(57) ABSTRACT

A composition for dyeing keratinous fiber which includes incorporated therein an oxidative color-developing substance, an enzyme which reacts with oxygen as a substrate but does not evolve hydrogen peroxide, and a weak reducing agent.

12 Claims, No Drawings

COMPOSITIONS FOR DYEING KERATINOUS FIBER

This application is the national phase under 35 U.S.C. §371 of PCT International Application No. PCT/JP00/08525 which has an International filing date of Dec. 1, 2000 which designated the United States of America, the entire contents of which are hereby incorporated by reference.

TECHNICAL FIELD

The present invention relates to a composition for dyeing keratinous fiber which comprises an oxidative color-developing substance, an enzyme which reacts with oxygen as a substrate but does not evolve hydrogen peroxide, and a weak reducing agent. More particularly, the present invention relates to a composition for dyeing keratinous fiber which is well protected from discoloration of compositions with time.

BACKGROUND ART

There are compositions for dyeing keratinous fiber which perform their function by oxidation of an oxidative color-developing substance, which include, for example, hair dyes and eyebrow dyes. Such compositions for dyeing keratinous fiber conventionally employ hydrogen peroxide as an oxidizing agent. Therefore, most of them are of two-pack type. That is, the oxidative color-developing agent and the oxidizing agent are stored in separate containers, and they are mixed together for reaction at the time of use. The composition of this type is inconvenient to use, and there has been a demand for improvement in their usability. Moreover, it is known that hydrogen peroxide damages keratinous fiber such as hair, and this has produced dissatisfaction with consumers.

One way to address the above-mentioned problem is to replace hydrogen peroxide by an oxidase (as an oxidizing agent) which is previously mixed with an oxidative color-developing substance. The oxidase may be peroxidase (as disclosed in Japanese Patent Laid-open Nos. Sho 47-10400 and Sho 53-32132), laccase (as disclosed in U.S. Pat. No. 3,251,742 and Japanese Patent Laid-open No. Hei 6-172145), or uricase (as disclosed in Japanese Patent Laid-open No. Sho 63-246313).

Among these disclosed technologies, however, the peroxidase-containing composition needs hydrogen peroxide on account of the characteristic properties of peroxidase, and hence the resulting composition cannot be of one-pack type. The uricase-containing composition can be of one-pack type, but it does not solve the basic problem with the use of hydrogen peroxide evolved by the enzyme reaction.

By contrast, in the case where an oxidase which reacts with oxygen as a substrate but does not evolve hydrogen peroxide is used, the composition for dyeing keratinous fiber can be of one-pack type. In addition, such a composition is useful because it does not evolve hydrogen peroxide which damages keratinous fiber (See Japanese Patent Laid-open No. Hei 11-60454). However, it suffers the disadvantage of getting discolored with time during storage, because the enzyme (as a protein) is unstable under the high-temperature high-humidity condition. Therefore, the resulting composition does not permit the enzyme to fully perform its function, and its discoloration is a serious drawback.

It has been known that the above-mentioned discoloration can be effectively eliminated by incorporation with a reducing agent (See "Science of Wave" issued by Shinbiyo Shuppan Co., Ltd.). Improvement of storage stability of enzyme is disclosed in Japanese Patent Laid-open No. Hei 8-175935 (for catalase) and Japanese Patent Laid-open No. Hei 8-217652 (for uricase). These disclosed technologies employ a reducing agent, however, incorporation of a reducing agent into the composition for dyeing keratinous fiber poses a problem. That is, a strong reducing agent lowers the enzyme activity, thereby deteriorating dyeing power, and a weak reducing agent does not fully protect the composition from discoloration.

DISCLOSURE OF INVENTION

The present invention was completed in view of the foregoing, and it is accordingly an object of the present invention to provide a composition for dyeing keratinous fiber which does not damage keratinous fiber, protects itself from discoloration during storage, exhibits good enzyme action, and allows consumers easy use.

The present inventors' investigation to achieve the above-mentioned object revealed that if a composition for dyeing keratinous fiber, which is composed of an oxidative color-developing substance and an enzyme which reacts with oxygen as a substrate but does not evolve hydrogen peroxide, is incorporated with a weak reducing agent, the resulting composition has greatly improved stability with time, as demonstrated in the following Examples. That is, the composition protects itself from discoloration with time (particularly during storage at high temperatures) without deteriorating dyeing power, and remains free from insoluble aggregates during storage. The investigation revealed further that the composition has better storage stability upon incorporation with cyclodextrin. The present invention is based on these findings.

Accordingly, the present invention is directed to a composition for dyeing keratinous fiber which comprises incorporated therein an oxidative color-developing substance, an enzyme which reacts with oxygen as a substrate but does not evolve hydrogen peroxide, and a weak reducing agent. The composition should preferably be incorporated with cyclodextrin.

BEST MODE FOR CARRYING OUT THE INVENTION

In what follows, the invention will be described in more detail. According to the present invention, the composition for dyeing keratinous fiber comprises incorporated therein an oxidative color-developing substance, an enzyme which reacts with oxygen as a substrate but does not evolve hydrogen peroxide, and a weak reducing agent. It should preferably be additionally incorporated with cyclodextrin.

According to the present invention, the composition for dyeing keratinous fiber is not restricted in the form as a commodity, but it may also be in the form of reactive hair dye or reactive dye for eyebrows, eyelashes, and body hair. Regardless of the commodity type, the composition should be a solution or an emulsion (which may contain a propellant) in which the enzyme is dissolved. The composition at the time of use may be in the form of foam, cream, or clear gel.

According to the present invention, the oxidative color-developing substance is not specifically restricted in its kind, but Colorant precursors, developers, and direct dyes may also be used. It includes all ordinary oxidation dyes, such as those listed in the standard for raw materials of hair dyes (The 3rd revised edition, issued in May 1985 by Japan Hair Color Industry Association, Japan Hair Dye Industry Conference). Their typical examples are as follows.

5-amino-o-cresol, o-aminophenol, m-aminophenol, p-aminophenol, 2,6-diaminopyridine, 5-(2-hydroxyethylamino)-2-methylphenol, N,N-bis(2-hydroxyethyl)-p-phenylenediamine, p-nitro-o-phenylenediamine, p-phenylenediamine, m-phenylenediamine, N-phenyl-p-phenylenediamine, catechol, resorcin, hydroquinone, 3,3'-iminodiphenol, diphenylamine, 2-hydroxy-5-nitro-2',4'-diaminobenzene.sodium sulfate, toluene-2,5-diamine, 2-(2'-hydroxyethylamino)-5-aminotoluene, N,N-bis(2-hydroxyethyl)-p-phenylenediamine sulfate, 5-amino-o-cresol.sulfate, p-aminophenol.sulfate, o-chloro-p-phenylenediamine.sulfate, 2-(2'-hydroxyethylamine)-5-aminotoluene.sulfate, 4,4'-diaminodiphenylamine.sulfate, p-methylaminophenyl.sulfate, p-phenylenediamine.sulfate, m-phenylenediamine.sulfate, toluene-2,5-diamine.sulfate, 2,4-diaminophenoxyethanol.hydrochloride, toluene-2,5-diamine.hydrochloride, m-phenylenediamine.hydrochloride, 2,4-diaminophenyl.hydrochloride, N-phenyl-p-phenylenediamine.hydrochloride, 2,4-diaminophenol.hydrochloride, N-phenyl-p-phenylenediamine.hydrochloride, N-phenyl-p-phenylenediamine acetate, 1,5-hyroxynaphthalene, toluene-3,4-diamine, p-methylaminophenol, N,N'-bis(4-aminophenyl)-2,5-diamino-1,4-quinonedimine, o-aminophenol.sulfate, 2,4-diaminophenol.sulfate, m-aminophenol.sulfate, 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, (-naphthol, 1,5-dihydroxynaphthelene, pyrogallol, phloroglucin, picric acid, picramic acid, sodium picramate, p-aminophenylsulfamic acid, 2-amino-5-nitrophenol.sulfate, nitro-p-phenylenediamine.sulfate, p-nitro-o-phenylenediamine.sulfate, and p-nitro-m-phenylenediamine.sulfate.

Of these examples, the following are particularly preferable:
p-phenylenediamine or salt thereof, toluene-2,5-diamine or salt thereof, p-aminophenol, 5-amino-o-cresol, p-methylaminophenol, 5-amino-o-cresol, p-methylaminophenol sulfate, m-aminophenol, p-nitro-o-phenylenediamine, 2,6-diaminopyridine, resorcinol, o-aminophenol, and m-phenylenediamine.

In addition, it is also possible to use various oxidation dyes (new compounds or oxidative base compounds) and couplers which are disclosed in the following international applications filed by Loreal Co., Ltd. They are listed below for reference:
WO99/36034, WO99/36035, WO99/36036, WO99/36037, WO99/36038, WO99/36039, WO99/36040, WO99/36041, WO99/36042, WO99/36043, WO99/36044, WO99/36045, and WO99/36046.

Examples of the oxidative base compounds include paraphenylenediamine, double base compounds, p-aminophenols, o-aminophenols, and heterocyclic oxidative base compounds.

The p-phenylenediamine which is desirable as the oxidative base compound to be incorporated into the composition of the present invention includes those compounds and acid adducts (or acid salts) thereof which are represented by the following general formula (1).

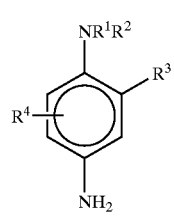

(1)

$R^1$ denotes a hydrogen atom, C1–4 alkyl group, C1–4 monohydroxyalkyl group, C2–4 polyhydroxyalkyl group, (C1–4)alkoxy(C1–4)alkyl group, and C1–4 alkyl group substituted with a nitrogen-containing group, phenyl group, or 4'-aminophenyl group; $R^2$ denotes a hydrogen atom, C1–4 alkyl group, C1–4 monohydroxyalkyl group, C2–4 polyhydroxyalkyl group, (C1–4)alkoxy(C1–4)alkyl group, and C1–4 alkyl group substituted with a nitrogen-containing group; $R^3$ denotes a hydrogen atom, halogen atom (such as chlorine, bromine, iodine, and fluorine), C1–4 alkyl group, C1–4 hydroxyalkyl group, C1–4 hydroxyalkoxyl group, C1–4 acetylaminoalkoxyl group, C1–4 mesylaminoalkoxyl group, and C1–4 carbamoylaminoalkoxyl group; and $R^4$ denotes a hydrogen atom, halogen atom, or C1–4 alkyl group.

The nitrogen-containing group in the general formula (1) includes, for example, amino group, mono(C1–4) alkylamino group, di(C1–4)alkylamino group, tri(C1–4) alkylamino group, monohydroxy(C1–4)alkylamino group, imidazolinium, and ammonium.

Typical examples of the paraphenylenediamine in the general formula (1) above include the following:
Paraphenylenediamine, paratolenediamine, 2-chloroparaphenyenediamine, 2,3-dimethylparaphenylenediamine, 2,6-dimethylparaphenylenediamine, 2,6diethylparaphenylenediamine, 2,5-dimethylparaphenylenediamine, N,N-dimethylparaphenylenediamine, N,N-diethylparaphenylenediamine, N,N-dipropylparaphenylenediamine, 4-amino-N,N-diethyl-3-methylaniline, N,N-bis(β-hydroxyethyl) paraphenylenediamine, 4-N,N-bis(β-hydroxyethyl) amino-2-methylaniline, 4-N,N-bis(β-hydroxyethyl) amino-2-chloroaniline, 2-β-hydroxyethylparaphenylenediamine, 2-fluoroparaphenylenediamine, 2-isopropylparaphenylenediamine, N-(β-hydroxypropyl) paraphenylenediamine, 2-hydroxymethylparaphenylenediamine, N,N-dimethyl-4-methylparaphenylenediamine, N,N-(ethyl-β-hydroxyethyl)paraphenylenediamine, N-(β,γ-dihydroxypropyl)paraphenylenediamine, N-(4'-aminophenyl)paraphenylenediamine, N-phenylparaphenylenediamine, 2-β-hydroxyethyloxyparaphenylenediamine, 2-β-acetylaminoethyloxyparaphenylenediamine, N-(β-methoxyethyl)paraphenylenedianine, and salts thereof.

Of the paraphenylenediamines in the general formula (1) above, those listed below are particularly preferable:
Paraphenylenediamine, paratolylenediamine, 2-isopropylparaphenylenediamine, 2-β-hydroxyethylparaphenylenediamine, 2-β-hydroxyethyloxyparaphenylenediamine, 2,6-dimethylparaphenylenediamine, 2,3-dimethylparaphenylenediamine, N,N-bis(β-hydroxyethyl) paraphenylenediamine, 2-chloroparaphenylenediamine, 2-β-acetylaminoethylparaphenylenediamine, and salts thereof.

The term "double base compound" as used in the present invention implies any compound which contains at least two aromatic rings which are cross-linked by an amino group and/or hydroxyl group.

The double base compound that can be incorporated into the composition of the present invention includes the compounds and acid salts thereof represented by the general formula (2) below.

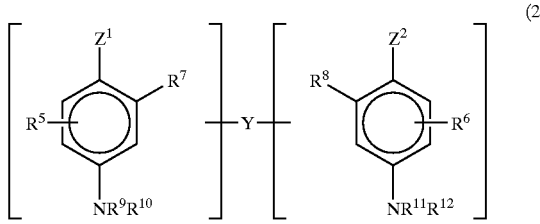

(2)

$Z^1$ and $Z^2$ (which may be identical or different) each denotes a hydrogen atom, hydroxyl group, or amino group, which may be substituted with a C1–4 alkyl group or a cross-linking group Y. The cross-linking group Y is a C1–14 linear or branched alkylene group, which may have one or more nitrogen-containing groups and/or one or more heteroatoms (such as oxygen, sulfur, and nitrogen) interposed or substituted. In addition, it may be substituted with one or more hydroxyl groups or C1–6 alkoxyl groups.

$R^5$ and $R^6$ each denotes any of hydrogen atom, halogen atom, C1–4 alkyl group, C1–4 monohydroxyalkyl group, C2–4 polyhydroxyalkyl group, C1–4 aminoalkyl group, or cross-linking group Y; $R^7$, $R^8$, $R^9$, $R^{10}$, $R^{11}$ (which may be identical or different) each denotes a hydrogen atom, cross-linking group Y, or C1–4 alkyl group.)

It is assumed that the compound represented by the general formula (2) above has one cross-linking group per molecule.

The nitrogen-containing group in the general formula (2) above includes, for example, an amino group, mono(C1–4)alkylamino group, di(C1–4)alkylamino group, tri(C1–4)alkylamino group, monohydroxy(C1–4)alkylamino group, imidazolinium, and ammonium.

The double base compound in the general formula (2) above is exemplified by the following:
N,N=bis-(β-hydroxyethyl)N,N'=bis-(4'-aminophenyl)-1,3 diaminopropanol, N,N=bis-(β-hydroxyethyl)N,N'=bis-(4'-aminophenyl)ethylenediamine, N,N=bis-(4'-aminophenyl)tetramethylenediamine, N,N'-bis-(β-hydroxyethyl)-N,N'-bis-(4-aminophenyl)tetramethylenediamine, N,N'-bis-(4-methylaminophenyl)tetramethylenediamine, N,N'-bis-(ethyl)N,N'-bis-(4-amino 3-methylphenyl)ethylenediamine, 1,8-bis-(2,5-diaminophenoxy)-3,5-dioxaoctane, and acid salts thereof.

Of the above-mentioned examples in the general formula (2), the following double base compounds are particularly preferable:
N,N-bis-(β-hydroxyethyl)N,N'-bis-(4'-aminophenyl)1,3 diaminopropanol, 1,8-bis-(2,5-diaminophenoxy)-3,5-dioxaoctane, and acid salts thereof.

The oxidative base compound (or p-aminophenol) that can be incorporated into the composition of the present invention includes those compounds and acid salts thereof which are represented by the general formula (3) below.

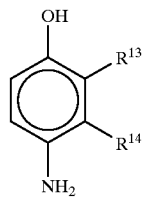

(3)

$R^{13}$ denotes a hydrogen atom, halogen atom, C1–4 alkyl group, C1–4 monohydroxyalkyl group, (C1–4)alkoxyl group, C1–4 aminoalkyl group, or (C1–4)hydroxyalkyl (C1–4)aminoalkyl group; $R^{14}$ denotes a hydrogen atom, halogen atom, C1–4 alkyl group, C1–4 monohydroxyalkyl group, C2–4 polyhydroxyalkyl group, C1–4 aminoalkyl group, C1–4 cyanoalkyl group, or (C1–4)alkoxy(C1–4)alkyl group. At least either of $R^{13}$ and $R^{14}$ is a hydrogen atom.

Typical examples of the p-aminophenol in the general formula (3) above includes the following:
p-aminophenol, 4-amino 3-methylphenol, 4-amino 3-fluorophenol, 4-amino 3-hydroxymethylphenol, 4-amino 2-methylphenol, 4-amino 2-hydroxymethyphenol, 4-amino 2-methoxyphenol, 4-amino 2-amionphenol, 4-amino 2-(β-hydroxyethylaminoethyl)phenol, 4-mino 2-fluorophenol, and acid salts thereof.

The oxidative base compound (or o-aminophenol) that can be incorporated into the composition of the present invention includes, for example, 2-aminophenol, 2-amino 5-methylphenol, 2-amino 6-methylphenol, 5-acetamide 2-aminophenol, and acid salts thereof.

The oxidative base compound (or heterocyclic base compound) that can be incorporated into the composition of the present invention includes, for example, pyridine derivative, pyrimidine derivatives, pyrazole derivatives, pyrazolopyrimidine derivatives, and acid salts thereof. The above-mentioned pyridine derivatives includes those compounds mentioned in GB-PS1026978 and GB-PS1153196, such as 2,5-diaminopyridine, 2-(4-methoxyphenyl)amino 3-aminopyridine, 2,3-diamino 6-methoxypyridine, 2-(β-methoxyethyl)amino 3-amino 6-methoxypyridine, 3,4-diaminopyridine, and acid salts thereof.

Examples of the above-mentioned pyrimidine derivatives include those compounds mentioned in German Patent No. DE2359399, Japanese Patent Nos. JP88-169571 and JP91-333495, and International Laid-open No. WO96/15765, such as 2,4,5,6-tetraminopyridine, 4-hydroxy 2,5,6-triaminopyridine, 2-hydroxy 4,5,6-triaminopyridine, 2,4-dihydroxy 5,6-diaminopyridine, 2,5,6-triaminopyridine, and acid salts thereof.

Examples of the above-mentioned pyrazole derivatives include those compounds mentioned in German Patent Nos. DE3843892, DE4133957, DE19543988, International Laid-open Nos. WO94/08969 and WO94/08970, and French Patent No. FR-A-2733, as they are listed below:
4,5-diamino 1-methylpyrazole, 3,4-diaminopyrazole, 4,5-diamino 1-(4'-chlorobenzylpyrazole), 4,5-diamino 1,3-dimethylpyrazole, 4,5-diamino 3-methyl-1-phenylpyrazole, 4,5 diamino 1-methyl 3-phenylpyrazole, 4-amino 1,3 dimethyl 5-hydrazionopyrazole, 1-benzyl 4,5-diamino 3-methylpyrazole, 4,5-diamono 3-tert-butyl-1-methylpyrazole, 4,5-diamono 1-tert-butyl 3-methylpyrazole, 4,5-diamino 1-(β-hydroxyethyl)-3-methylpyrazole, 4,5-diamino 1-ethyl 3-methylpyrazole, 4,5-diamino-3-(4'-methoxyphenyl)methylpyrazole, 4,5-diamono 1-ethyl 3-hydroxymethylpyrazole, 4,5-diamino 3-hydroxymethyl 1-methylpyrazole, 4,5-diamino 3-hydroxymethyl 1-isopropylpyrazole, 4,5-diamino 3-methyl 1-ispropylpyrazole, 4-amino 5-(2'-aminoethyl) amino 1,3-dimethylpyrazole, 3,4,5-triaminopyrazole, 1-methyl 3,4,5-triaminopyrazole, 3,5-diamino 1-methyl 4-methylaminopyrazole, 3,5-diamino 4-(β-hydroxyethyl) amino 1-methylpyrazole, and acid salts thereof.

Examples of the above-mentioned pyrazolopyrimidine derivatives include pyrazole-[1,5,a]-pyrimidine derivative or acid salt thereof which is represented by the general formula (4) below. The derivatives include tautomers thereof if there exist tautomeric equilibrium.

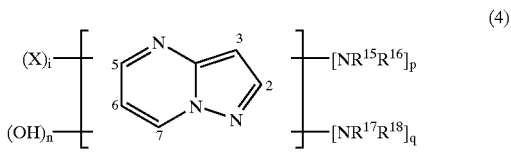

(4)

$R^{15}$, $R^{16}$, $R^{17}$, and $R^{18}$ (which may be identical or different) each denotes a hydrogen atom, C1–4 alkyl group, aryl group, C1–4 hydroxyalkyl group, C2–4 polyhydroxyalkyl group, (C1–4)alkoxy(C1–4)alkyl group, C1–4 aminoalkyl group (in which the amino group may be protected with an acetyl group, ureido group, or sulfonyl group), (C1–4)alkylamino(C1–4)alkyl group, di[(C1–4)alkyl]amino (C1–4)alkyl group (in which the dialkyl group may form a cyclic hydrocarbon group, 5- or 6-membered heterocyclic group), hydroxy(C1–4)alkyl group, or di[hydroxy(C1–4) alkyl]amino(C1–4)alkyl group.

The X groups (which may be identical or different) each denotes a hydrogen atom, C1–4 alkyl group, aryl group, C1–4 hydroxyalkyl group, C2–4 polyhydroxyalkyl group, amino(C1–4)alkyl group, (C1–4)alkyl(C1–4)aminoalkyl group, di[(C1–4)alkyl]amino(C1–4)alkyl group (in which the dialkyl group may form a cyclic hydrocarbon group, 5- or 6-membered heterocyclic group), hydroxy(C1–4)alkyl group, di[hydroxy(C1–4)alkyl]amino(C1–4)alkyl group, amino group, di[(C1–4)alkyl]amino(C1–4)alkyl group, halogen atom, carboxylic group, or sulfonic group.

i denotes 0, 1, or 3; p denotes 0 or 1; q denotes 0 or 1; and n denotes 0 or 1, provided that p+q is not 0. If p+q is 2, n denotes 0 and $NR^{15}R^{16}$ and $NR^{17}R^{18}$ are at any position of (2,3), (5,6), (6,7), (3,5), and (3,7). If p+q is 1, n denotes 1 and $NR^{15}R^{16}$ (or $NR^{17}R^{18}$) and the hydroxyl group are at any position of (2,3), (5,6), (6,7), (3,5), and (3,7).

In the case where the pyrazolo-[1,5,a]-pyrimidine derivative represented by the general formula (4) above has a hydroxyl group at any one position of 2, 5, and 7 (which is α position with respect to the nitrogen atom), there exists tautomeric equilibrium as represented by the following reaction formula.

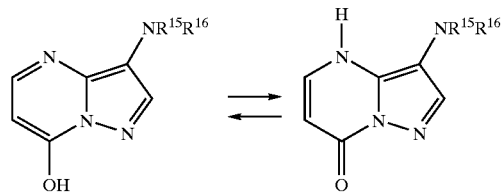

Examples of the pyrazolo-[1,5,a]-pyrimidine derivative represented by the general formula (4) above include the following:

Pyrazolo-[1,5,a]-pyrimidine-3,7-diamine, 2,5-dimethylpyrazolo-[1,5,a]-pyrimidine-3,7-diamine, pyrazolo-[1,5,a]-pyrimidine-3,5-diamine, 2,7-dimethylpyrazolo-[1,5,a]-pyrimidine-3,5-diamine, 3-aminopyrazolo-[1,5,a]-pyrimidine-7-ol, 3-aminopyrazolo-[1,5,a]-pyrimidine-5-ol, 2-(3-aminopyrazolo-[1,5,a]-pyrimidine-7-ylamino)-ethanol, 2-(7-aminopyrazolo-[1,5,a]-pyrimidine-3-ylamino)-ethanol, 2-[(3-aminopyrazolo-[1,5,a]-pyrimidine-7-yl)-(2-hydroxyethyl)-amino]ethanol, 2-[(7-aminopyrazolo-[1,5,a]-pyrimidine-3-yl)-(2-hydroxyethyl)-amino]ethanol, 5,6-dimethylpyrazolo-[1,5,a]-pyrimidine-3,7-diamine, 2,6-dimethylpyrazolo-[1,5,a]-pyrimidine-3,7-diamine, 2,5-N', N'-teteramethylpyrazolo-[1,5,a]-pyrimidine-3,7 diamine, and acid salts thereof, and tautomers thereof if there exist their tautomeric equilibrium.

The pyrazolo-[1,5,a]-pyrimidine derivative represented by the general formula (4) above can be synthesized by cyclization of aminopyrazole according to the method mentioned in the following literature:

(1) EP No. 628559, BEIERSDORF-LILLY
(2) R. Vishdu, H. Navedul, Indian J. Chem., 34b(6), 514, 1995.
(3) N. S. Ibrahim, K. U. Sadek, F. A. Abdel-Al, Arch. Pharm., 320, 240, 1987.
(4) R. H. Springeer, M. B. Scholten, D. E. O'Brien, T. Novinson, J. P. Miller, R. K. Robins, J. Med. Chem., 25, 235, 1982.
(5) T. Novinson, R. K. Robins, T. R. Matthews, J. Med. Chem., 20, 296, 1977.
(6) U.S. Pat. No. 3,907,799, ICN PHARMACEUTICAL The pyrazolo-[1,5,a]-pyrimidine derivative represented by the general formula (4) above can also be synthesized by cyclization of hydrazine according to the method mentioned in the following literature:

(1) A. McKillop, R. J. Kobilecki, Heterocycles, 6(9), 1355, 1977.
(2) E. Alcade, J. DeMendora, J. M. Macrcia-Marquina, C. Almera, J. Elguero, J. Heterocyclic Chem., 11(3), 423, 1974.
(3) K. Saito, I. Hori, M. Igarashi, H. Midorikawa, Bull. Chem. Soc. Japan, 47(2), 476, 1974.

The above-mentioned oxidative base compound should preferably be added in an amount of 0.0005 to 12%, particularly 0.005 to 6%, of the total amount of the composition of the present invention. (% means mass % hereinafter.)

The coupler that can be added to the composition of the present invention includes m-phenylenediamine, m-aminophenol, m-diphenol, heterocyclic coupler, and acid salts thereof, which are commonly used for oxidation hair dyes.

Examples of the coupler are listed below. 2-methyl-5-aminophenol, 5-N-(β-hydroxyethyl)-amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis-(2,4-diaminophenoxy)-propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-on, 1-phenyl-3-methyl-pyrazol-5-on, 2,6-dimethylpyrazole-[1,5b]-1,2,4-triazole, 2,6-dimethyl-[3,2-c]-1,2,4-triazole, 6-methylpyrazolo-[1,5-a]-benzimidazole, 6-methylpyrazolo-[1,5-a]-benzimidazole, and acid salts thereof.

Examples of the m-aminophenol include those compounds and acid salts thereof represented by the general formula (5) below.

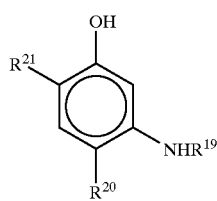

(5)

$R^{19}$ denotes a hydrogen atom, C1–4 alkyl group, C1–4 monohydroxyalkyl group, or C2–4 polyhydroxyalkyl group; $R^{20}$ denotes a hydrogen atom, C1–4 alkyl group, C1–4 alkoxyl group, or halogen atom (which is any of chlorine, iodine, bromine, and fluorine); and $R^{21}$ denotes a hydrogen atom, C1–4 alkyl group, C1–4 alkoxyl group, C1–4 monohydroxyalkyl group, C2–4 polyhydroxyalkyl group, C1–4 monohydroxyalkoxyl group, or C2–4 polyhydroxyalkoxyl group.

Typical examples of the m-aminophenol represented by the general formula (5) above are listed below. m-aminophenol, 5-amino-2-methoxyphenol, 5-amino-2-(β-hydroxyethoxy)-phenol, 5-amino-2-methylphenol, 5-N-(β-hydroxyethyl)amino-2-methylphenol, 5-N-(β-hydroxyethyl)amino-4-methoxy-2-methylphenol, 5-amino-4-methoxy-2-methylphenol, 5-amino-4-chloro-2-methylphenol, 5-amino-2,4-dimethoxyphenol, 5-(γ-hydroxypropylamino)-2-methylphenol, and acid salts thereof.

The m-phenylenediamine used as the coupler in the composition of the present invention should preferably be any compound or acid salt thereof represented by the general formula (6) below.

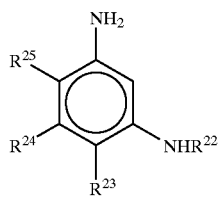

(6)

$R^{22}$ denotes a hydrogen atom, C1–4 alkyl group, C1–4 monohydroxyalkyl group, or C2–4 polyhydroxyalkyl group; $R^{23}$ and $R^{24}$ (which may be identical or different) each denotes a hydrogen atom, C1–4 alkyl group, C1–4 monohydroxyalkyl group, or C2–4 polyhydroxyalkyl group; and $R^{25}$ denotes a hydrogen atom, C1–4 alkoxyl group, C1–4 aminoalkoxyl group, C1–4 monohydroxyalkoxyl group, C2–4 polyhydroxyalkoxyl group, or 2,4-diaminophenoxyalkoxyl group.

Typical examples of the m-phenylenediamine represented by the general formula (6) above are listed below:
2,4-diaminobenzene, 3,5-diamino-1-ethyl-2-methoxybenzene, 3,5-diamino-2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-5-(β-hydroxyethyloxy)-1-methylbenzene, 2,4-diamino-1-(β,γ-dihydroxy-propyloxy)benzene, 2,4-diamino-1-(β-hydroxyethyloxy)benzene, 2-amino-4-N-(β-hydroxyethyl)-amino-1-methoxybenzene, and acid salts thereof.

The m-diphenyl used as the coupler in the composition of the present invention should preferably be any compound or acid salt thereof represented by the general formula (7) below.

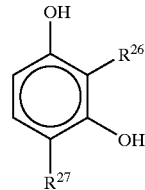

(7)

$R^{26}$ and $R^{27}$ (which may be identical or different) each denotes a hydrogen atom, C1–4 alkyl group, or halogen atom which is any of chlorine, iodine, bromine, and fluorine.

Typical examples of the m-diphenol represented by the general formula (7) above are: 1,3-dihydroxybenzene, 2-methyl-1,3-dihydroxybenzene, 4-chloro-1,3-dihydroxybenzene, 2-chloro-1,3-dihydroxybenzene, and acid salts thereof.

The heterocyclic coupler used as the coupler in the composition of the present invention includes the following:
Benzimidazole derivatives, benzmorpholine derivatives, sesamol derivatives, pyrazolo-azole derivatives, pyrroloazole derivatives, imidazole-azole derivatives, pyrazolopyrimidine derivatives, pyrazolin-3,5-dion derivatives, pyrrolo-[3,2d]-oxazole derivatives, pyrazol[3,4d]thiazole derivatives, thiazolo-azole S-oxide derivatives, thiazolo-azole S,S-dioxide derivative, and acid salts thereof.

The heterocyclic coupler that can be used as the coupler in the composition of the present invention includes the following:
Benzimidazole derivatives, benzmorpholine derivatives, sesamol derivatives, pyrazolo-azole derivatives, pyrroloazole derivatives, imidazole-azole derivatives, pyrazolopyrimidine derivatives, pyrazolin-3,5-dion derivatives, pyrrolo-[3,2d]-oxazole derivatives, pyrazolo[3,4d]-thiazole derivatives, thiazolo-azole S-oxide derivatives, thiazolo-azole S,S-dioxide derivatives, and acid salts thereof.

The benzimidazole derivative as the heterocyclic coupler that can be added to the composition of the present invention includes any compound and acid salts thereof represented by the general formula (8) below.

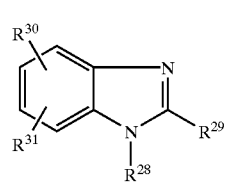

(8)

$R^{18}$ denotes a hydrogen atom or C1–4 alkyl group; $R^{29}$ denotes a hydrogen atom, C1–4 alkyl group, or phenyl group; and $R^{30}$ denotes a hydrogen atom, methoxy group, or C1–4 alkyl group. If $R^{30}$ is an amino group, it is at the fourth position; if $R^{30}$ is at the fourth position, $R^{31}$ is at the seventh position; and if $R^{30}$ is at the fifth position, $R^{31}$ is at the sixth position.

Typical examples of the benzimidazole derivative represented by the general formula (8) above are listed below:
4-hydroxybenzimidazol, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole, 5,6-dimethoxybenzimidazole, and acid salts thereof.

The benzomorpholine derivative as the heterocyclic coupler that can be added to the composition of the present invention includes any compound and acid salts thereof represented by the general formula (9) below.

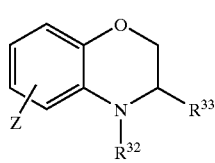

(9)

$R^{32}$ and $R^{33}$ (which may be identical or different) each denotes a hydrogen atom, C1–4 alkyl group, C1–4 monohydroxyalkyl group, C2–4 polyhydroxyalkyl group, (C1–4)alkoxy(C1–4)alkyl group, nitrogen-containing group, or phenyl group; and Z denotes a hydroxyl group or amino group.

Typical examples of the benzomorpholine derivative represented by the general formula (9) above include 6-hydroxy 1,4-benzomorpholine, N-methyl 6-hydroxy-1,4-benzomorpholine, 6-amino 1,4-benzomorpholine, and acid salts thereof.

The sesamol derivative as the heterocyclic coupler that can be added to the composition of the present invention includes any compound and acid salts thereof represented by the general formula (10) below.

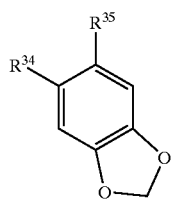

(10)

$R^{34}$ denotes a hydroxyl group, amino group, C1–4 alkylamino group, C1–4 monohydroxyalkylamino group, or C2–4 polyhydroxyalkylamino group; and $R^{35}$ denotes a hydrogen atom, halogen atom, or C1–4 alkoxyl group.

Typical examples of the sesamol derivative represented by the general formula (10) above include 2-bromo 4,5-methyleneoxyaniline, 2-methoxy 4,5-methyleneoxyaniline, 2-(β-hydroxyethyl)amino 4,5-methylenedioxybenzene, and acid salts thereof.

The pyrazole-azole derivative as the heterocyclic coupler that can be added to the composition of the present invention includes those compounds mentioned in the following patents and literatures:
Patents: FR-2075583, EP-A-119860, EP-A-285274, EP-A-244160, EP-A-578248, GB 1458377, U.S. Pat. No. 3,277,554, U.S. Pat. No. 3,419,391, U.S. Pat. No. 3,061,432, U.S. Pat. No. 4,500,630, U.S. Pat. No. 3,725,067, U.S. Pat. No. 3,926,631, U.S. Pat. No. 5,457,210, JP 84/99437, JP 83/42045, JP 84/162548, JP 84/171956, JP 85/33552, JP 85/43659, JP 85/172982, and JP 85/190779.
Literatures: Chem. Ber. 32, 797 (1899), Chem. Ber. 89, 2550, (1956), J. Chem. Soc. Perkin Trans., 2047, (1977), J. Prakt. Chem., 320, 533, (1978).

Typical examples of the above-mentioned pyrazolo-azole derivative are listed below:
2-methylpyrazolo [1,5-b]-1,2,4-triazole, 2-ethylpyrazolo [1,5-b]-1,2,4-triazole, 2-isopropylpyrazolo [1,5-b]-1,2,4-triazole, 2-phenylpyrzolo [1,5-b]-1,2,4-triazole, 2,6-dimethylpyrazolo [1,5-b]-1,2,4-triazole, 7-chloro 2,6-dimethylpyrazolo [1,5-b]-1,2,4-triazole, 3,6-dimethylpyrazolo [3,2-c]-1,2,4-triazole, 6-phenyl-3-methylthiopyrazolo [3,2-c]-1,2,4-triazole, 6-aminopyrazolo [1,5,a]-benzimidazole, and acid derivative thereof.

The pyrrolo-azole derivative as the heterocyclic coupler that can be added to the composition of the present invention includes those compounds mentioned in the following patents and literatures.
Patents: U.S. Pat. No. 5,256,526, EP-A-557851, EP-A-577248, EP-A-578248, EP-A-518238, EP-A-456226, EP-A-488909, EP-A-488248.
Literatures: D. R. Liljegren Ber. 1964, 3436; E. J. Browne, J. C. S., 1962, 5149; P. Magnus, J. A. C. S., 1990, 112, 2465; P. Magnus, J. A. C. S., 1987, 109, 2711; Angew. Chem. 1960, 72, 956, and Rec. Trav. Chim. 1961, 80, 1075.

Typical examples of the above-mentioned pyrrolo-azole derivative include 5-cyano-4-ethoxycarbonyl-8-methylpyrrolo [1,2-b]-1,2,4-triazole, 5-cyano-8-methyl-4-phenylpyrrolo [1,2-b]-1,2,4-triazole, 7-amino-6-ethoxycarbonylpyrrolo [1,2-a]-benzimidazole, and acid derivatives thereof.

The imidazolo-azole derivative as the heterocyclic coupler that can be added to the composition of the present invention includes those compounds mentioned in U.S. Pat. No. 5,441,863, JP 62-279337, JP 6-236011, and JP 7-92632.

Typical examples of the above-mentioned imidazoloazole derivative include 7,8-diaminoimidazolo-[3,2-a]-imidazole, 7,8-dicyano-4-methylimidazolo-[3,2-a]-imidazole, and acid salts thereof.

The pyrazolo-pyrimidine derivative as the heterocyclic coupler that can be added to the composition of the present invention includes those compounds mentioned in EP-A-304001.

Typical examples of the above-mentioned pyrazolo-pyrimidine derivative include the following. Pyrazolo-[1,5-a]pyrimidin-7-on, 2,5-dimethylpyrazolo-[1,5-a]pyrimidin-7-on, 2-methyl-6-ethoxycarbonylpyrazolo-[1,5-a] pyrimidin-7-on, 2-methyl-5-methoxymethylpyrazolo-[1,5-a]pyrimidin-7-on, 2-tert-butyl-5-fluoromethylpyrazolo-[1,5-a]pyrimidin-7-on, 2,7-dimethylpyrazolo-[1,5-a] pyrimidin-5-on, and acid derivatives thereof.

The pyrazolin-3,5-dione derivative as the heterocyclic coupler that can be added to the composition of the present invention includes those compounds mentioned in the following patents and literatures.
Patents: JP 7-36159, JP 7-84348, and U.S. Pat. No. 4,128,425.
Literatures:
(1) L. WYZGOWSKA, Acta. Pol. Pharm. 1982, 39(1–3), 83
(2) E. HANNING, Pharmazie, 1980, 35(4), 231
(3) M. H. ELNAGDI, BULL. Chem. Soc. Jap., 46(6), 1830, 1973
(4) G. CARDILLO, Gazz. Chim. Ital. 1966, 96, (8–9), 973.

Typical examples of the above-mentioned pyrazolin-3,5-dione derivative include 1,2-diphenylpyrazolin-3,5-dione, 1,2-diethylpyrazolin-3,5-dione, and acid salts thereof.

The pyrrolo-[3,2-d]-oxazole derivative as the heterocyclic coupler that can be added to the composition of the present invention includes those compounds mentioned in JP 7-325375 and J. Heterocycl. Chem. 16, 13, (1979).

The pyrazolo-[3,4-d]-thiazole derivative as the heterocyclic coupler that can be added to the composition of the present invention includes the compound mentioned in Japanese Patent Laid-open No. Hei 7-244361.

The thiazolo-azole S-oxide derivative and thiazolo-azole S,S-dioxide derivative as the heterocyclic coupler that can be added to the composition of the present invention include those compounds mentioned in the following patents and literatures:
(1) JP 7-98489
(2) Khim. Geterotsilk. Sodein, 1967, p. 93.
(3) J. Prakt. Chem., 318, 1976, p. 12.
(4) Indian J. Heterocycl. Chem. 1995, 5(2), 135.
(5) Acta. Pol. Pharm. 1995, 52(5), 415.
(6) Heterocycl. Commun. 1995, 1(4), 297.
(7) Arch. Pharm. (Weinheim, Ger.), 1994, 327(12), 825.

The above-mentioned coupler should be added in an amount of 0.0001 to 10%, preferably 0.005 to 5%, of the total amount of the composition of the present invention.

The composition of the present invention may optionally be incorporated with a cationic direct dye. The cationic direct dye that can be added to the composition of the present invention includes, for example, cationized aminoanthraquione dyes, cationized mono- or di-azo dyes, and cationized naphthoquinone dyes.

Typical examples of the above-mentioned dyes are listed below:
[8-[(p-aminphenyl)azo]-7-hydroxy-2-naphthyl]trimethylammonium chloride (synonymous with basic brown 16, arianol mahogany 306002 in color index), 3-[(4-amino-6-bromo-5,8-dihydro-1-hydroxy-8-imino-5-oxo-2-naphthalenyl)amino]-N,N,N-trimethylbenzenamium chloride (synonymous with basic blue 99, arianol steel blue 306004 in color index), 7-hydroxy-8-[(2-methoxyophenyl)azo]-N,N,N-trimethyl-2-naphthalenamium chloride (synonymous with basic red 76, arianol madar red in color index), [8-(4-amino-2-nitrophenyl)azo]-7-hydroxy-2-naphthyl]trimethyl ammonium chloride (cynonymous with basic brown 17, arianol siena brown 306001 in color index), 3-[(4,5-dihydro-3-methyl-5-oxo-1-phenyl-1H-pyrazol-4-yl)azo]-N,N,N-trimethylbenzenamium chloride (synonymous with basic yellow 57, arianol straw yellow 306005 in color index).

In addition, the above-mentioned cationic direct dye may be selected from the following.
(a) Those compounds represented by the general formula (11) below.

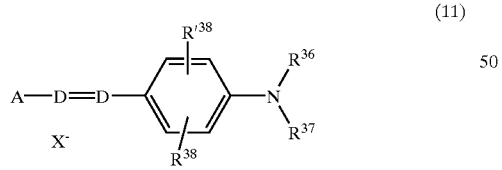

(11)

D denotes a nitrogen atom or —CH group; $R^{36}$ and $R^{37}$ (which may be identical or different) each denotes a hydrogen atom, C1–4 alkyl group (which may be substituted with any one of —CN, —OH, and —NH$_2$, or accompany a carbon atom and form a benzene ring or an oxygen-containing or nitrogen-containing hetero ring (with the ring optionally being substituted with one or more C1–4 alkyl group or 4'-aminopenyl group).

$R^{38}$ and $R'^{38}$ (which may be identical or different) each denotes a hydrogen atom, halogen atom selected from chlorine, bromine, iodine, and fluorine, cyano group, C1–4 alkoxyl group, or acetyloxy group; X⁻ denotes an anion (preferably chloride, methylsulfate, or acetate); and A denotes any of the following groups numbered A1 to A19.)

A1
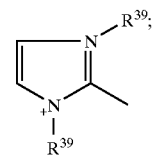

A2
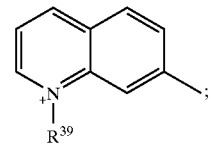

A3
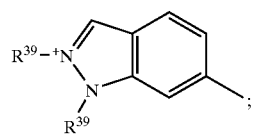

A4
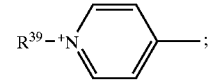

A5
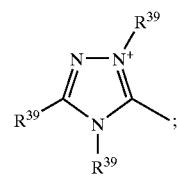

A6
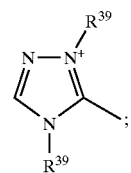

A7
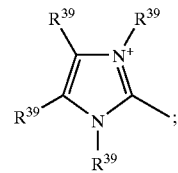

A8
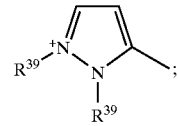

A9
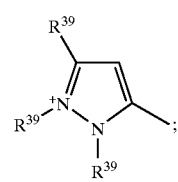

A10
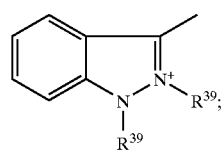

-continued

A11

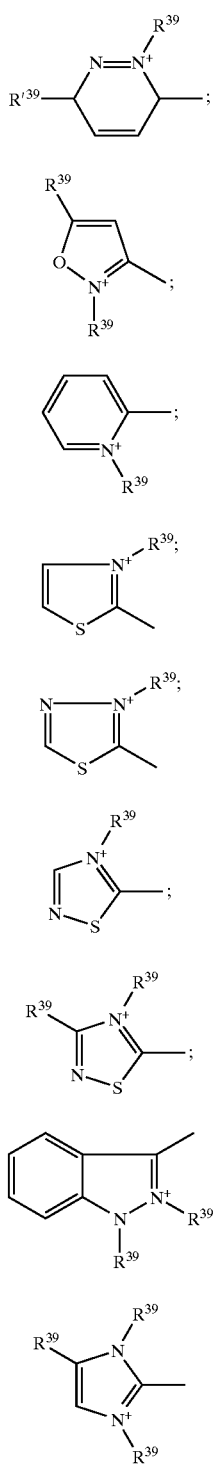

A12

A13

A14

A15

A16

A17

A18

A19

$R^{39}$ denotes a C1–4 alkyl group (which may be substituted with a hydroxyl group or C1–4 alkoxyl group); and $R'^{39}$ denotes a C1–4 alkoxyl group.

(b) Those compounds represented by the general formula (12) below.

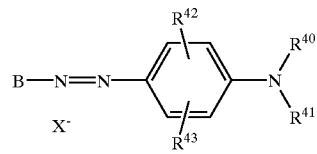

(12)

$R^{40}$ denotes a hydrogen atom, C1–4 alkyl group; $R^{41}$ denotes a hydrogen atom or alkyl group (which may be substituted with any one of —CN group, amino group, 4'-aminophenyl group) or $R^{41}$ may form an oxygen-containing and/or nitrogen-containing hetero aromatic ring with $R^{40}$ (this hetero aromatic ring may be substituted with a C1–4 alkyl group); $R^{42}$ and $R^{43}$ (which may be identical or different) each denotes a hydrogen atom, halogen atom selected from chlorine, bromine, iodine, and fluorine, C1–4 alkoxyl group, C1–4 alkoxyl group, or —CN group; X— denotes an anion (preferably chloride, methylsulfate, or acetate); and B denotes any one of the following groups numbered B1 to B6.

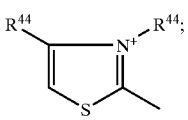

B1

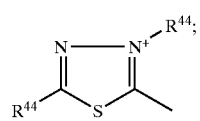

B2

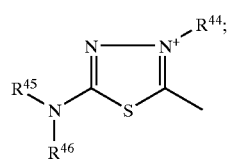

B3

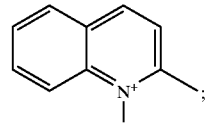

B4

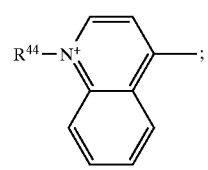

B5

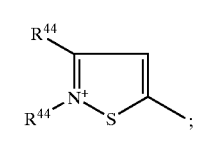

B6

$R^{44}$ denotes a C1–4 alkyl group, and $R^{45}$ and $R^{46}$ (which may be identical or different) each denotes a hydrogen atom or C1–4 alkyl group.

(c) Those compounds represented by the general formulas (13) and (13') below.

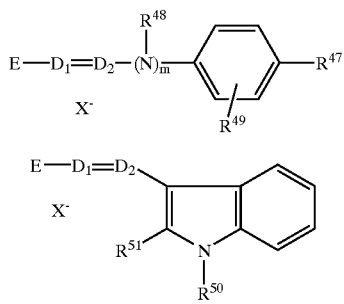
(13)

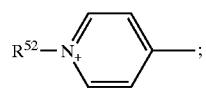 (13')

$R^{47}$ denotes a hydrogen atom, halogen atom selected from chlorine, bromine, iodine, and fluorine, amino group, C1–4 alkoxyl group, or acetyloxy group; $R^{48}$ denotes a hydrogen atom, C1–4 alkyl group, or heterocyclic ring containing carbon atoms (forming a benzene ring in the molecule) or oxygen atom (this hetero ring may be substituted with a C1–4 alkyl group); $R^{49}$ denotes a halogen atom selected from chlorine, bromine, iodine, and fluorine; $R^{50}$ and $R^{15}$ (which may be identical or different) each denotes a hydrogen atom or C1–4 alkyl group; $D_1$ and $D_2$ (which may be identical or different) each denotes a nitrogen atom or —CH group; m is 0 or 1. If $R^{47}$ is an unsubstituted amino group, both $D_1$ and $D_2$ denote a —CH group, and m is 0. X— denotes an anion, preferably chloride, methylsulfate, or acetate. E is any one of the following groups numbered E1 to E8.

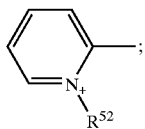 E1

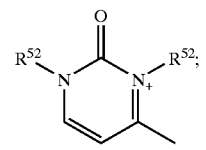 E2

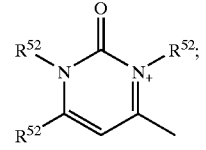 E3

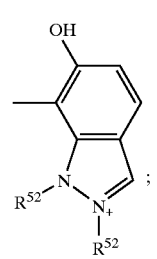 E4

E5

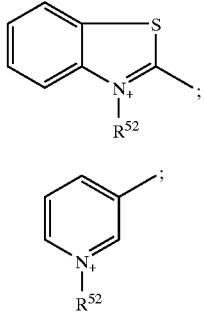
E6

E7

E8

$R^{52}$ denotes a C1–4 alkyl group.

If m is 0 and $D_1$ denotes a nitrogen atom, E denotes E9 given below.

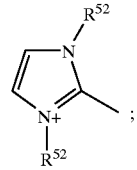 E9

$R^{52}$ denotes a C1–4 alkyl group.

The compounds represented by the general formulas (11), (12), (13), and (13') above as the cationic direct dye that can be added to the composition of the present invention include, for example, those compounds mentioned in WO 95/01772, WO 95/15144, and EP-A-0714954.

Typical examples of the compounds represented by the general formula (11) as the cationic direct dye that can be added to the composition of the present invention include those which are represented by the following structural formulas (11-1) to (11-52).

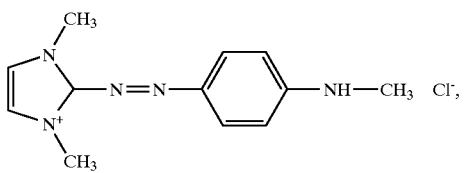 (11-1)

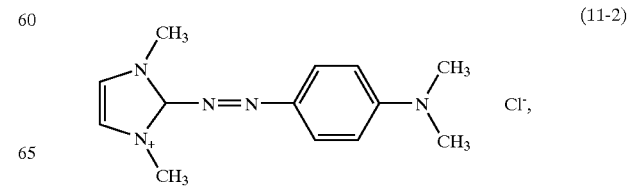 (11-2)

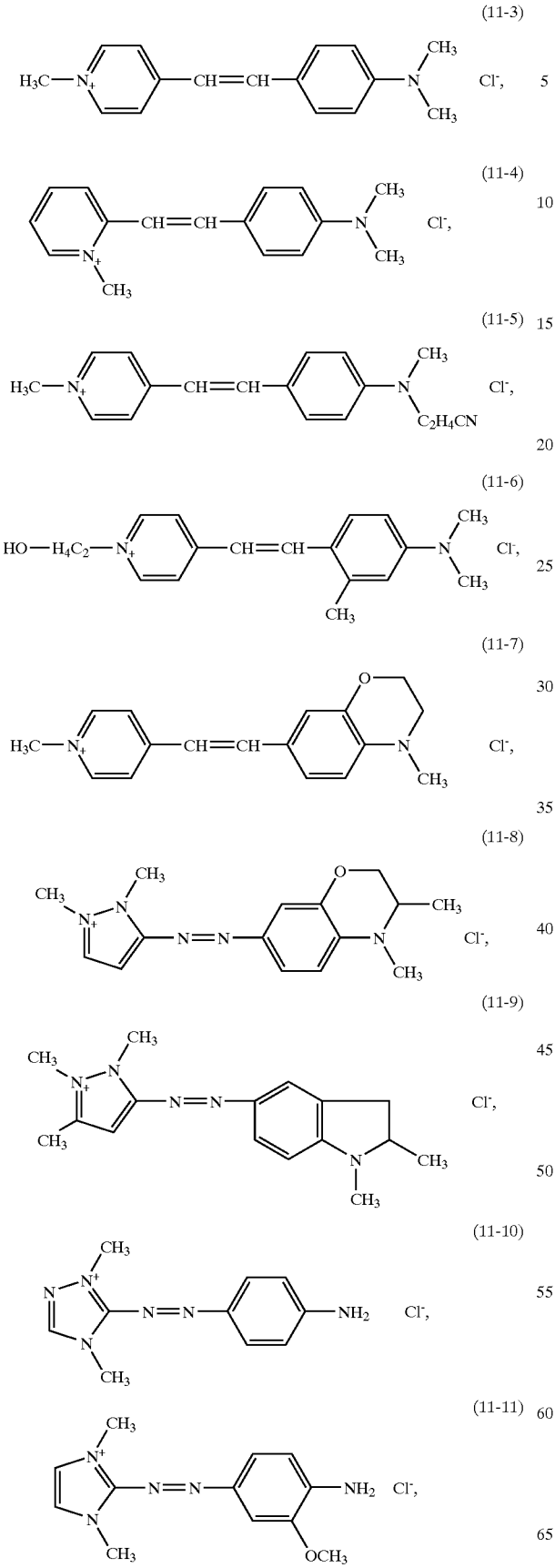
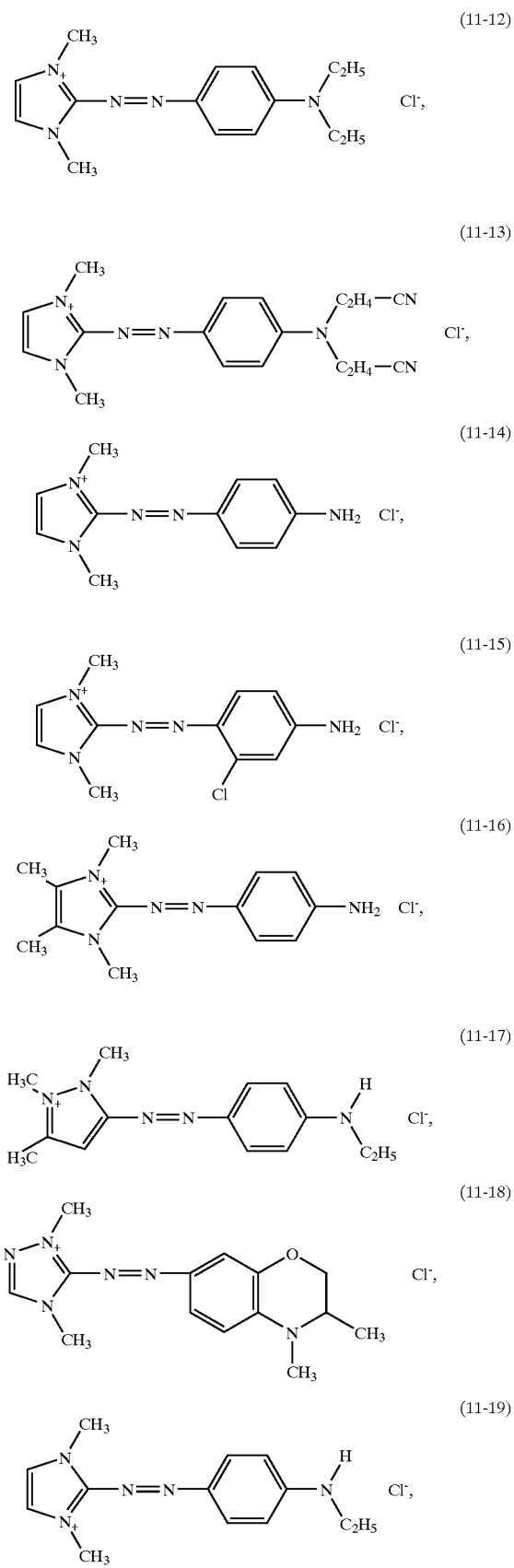

(11-20) 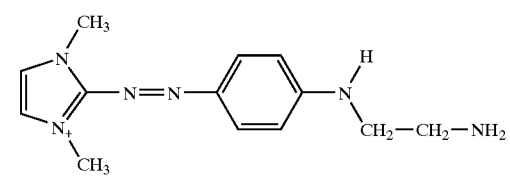 Cl⁻,
(11-21) 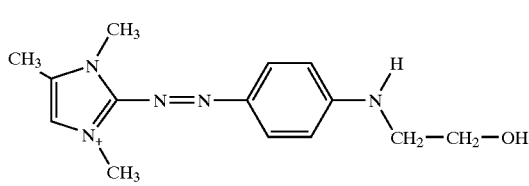 Cl⁻,
(11-22) 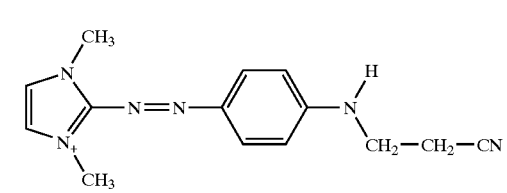 Cl⁻,
(11-23) 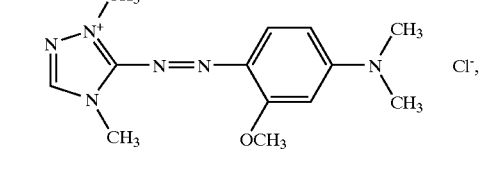 Cl⁻,
(11-24) 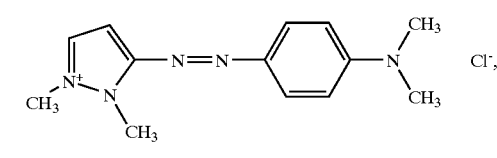 Cl⁻,
(11-25) 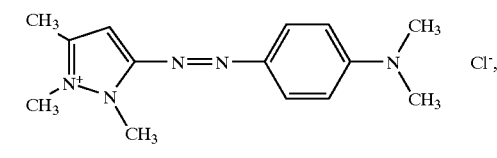 Cl⁻,
(11-26) 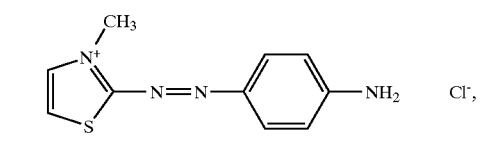 Cl⁻,
(11-27) 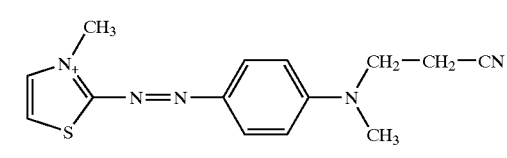 Cl⁻,
(11-28) 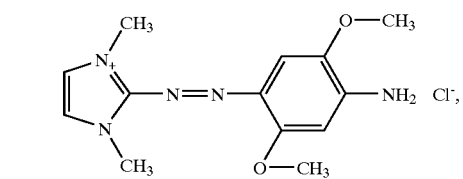 Cl⁻,
(11-29) 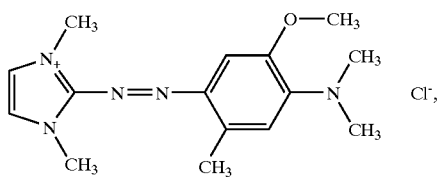 Cl⁻,
(11-30) 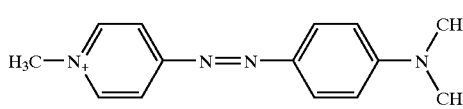 Cl⁻,
(11-31) 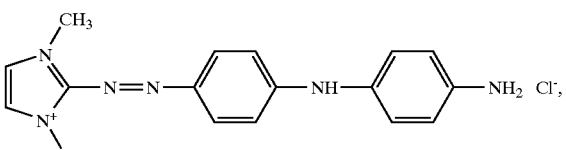 Cl⁻,
(11-32) 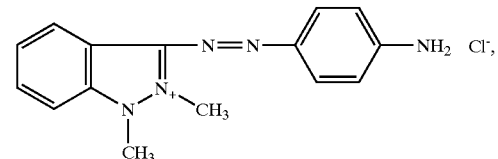 Cl⁻,
(11-33) 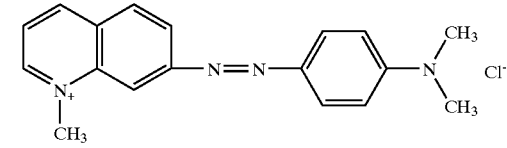 Cl⁻,
(11-34) 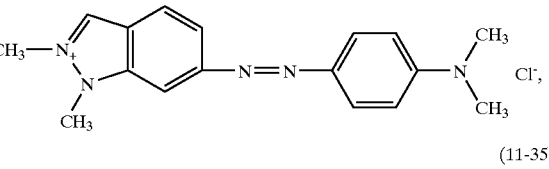 Cl⁻,
(11-35) 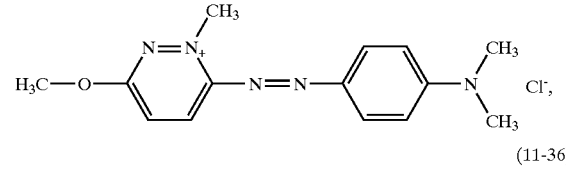 Cl⁻,
(11-36) 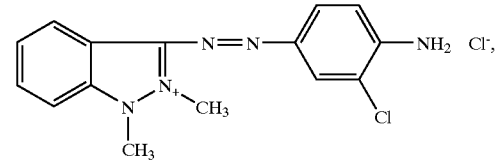 Cl⁻,
(11-37) 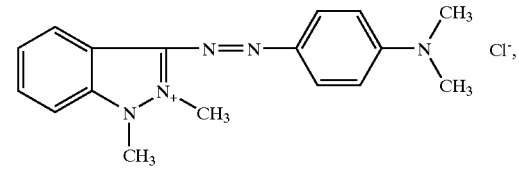 Cl⁻,

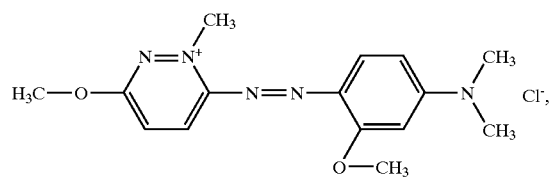
(11-38)

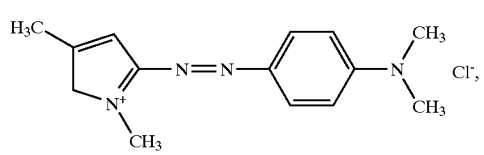
(11-39)

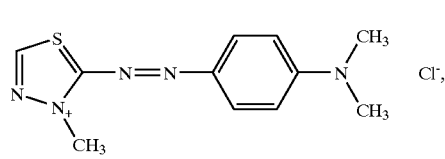
(11-40)

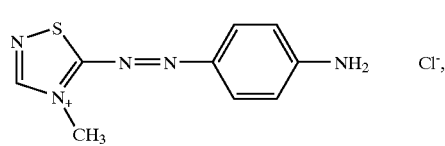
(11-41)

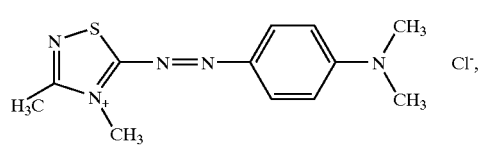
(11-42)

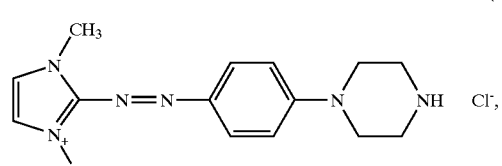
(11-43)

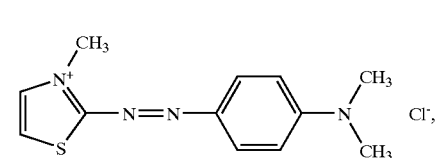
(11-44)

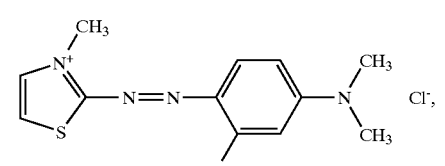
(11-45)

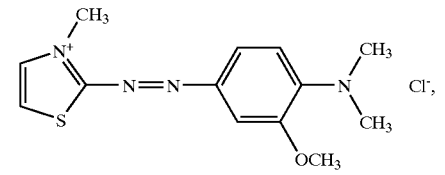
(11-46)

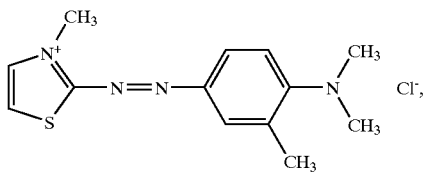
(11-47)

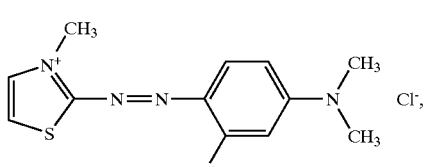
(11-48)

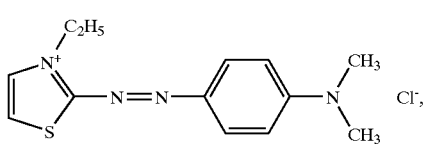
(11-49)

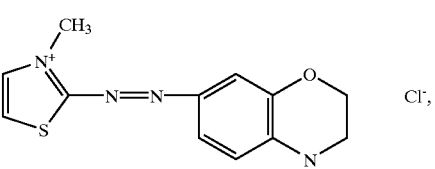
(11-50)

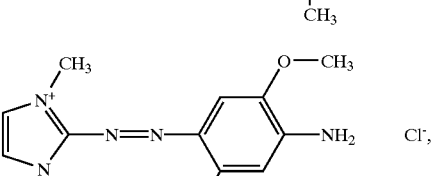
(11-51)

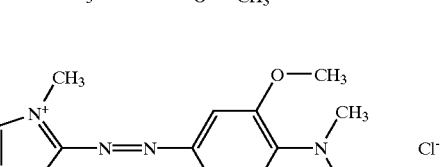
(11-52)

Of the compounds represented by the structural formulas (11-1) to (11-52) above, those which are represented by the structural formulas (11-1), (11-2), (11-4), (11-14), and (11-31) are particularly preferable.

Those compounds represented by the general formula (12) above as the cationic direct dye that can be added to the composition of the present invention include, for example, those compounds which are represented by the structural formulas (12-1) to (12—12) below. Of these compounds, those which are represented by the structural formulas (12-1) and (12—12) are particularly preferable.

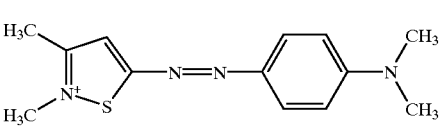
(12-1)

(12-2)
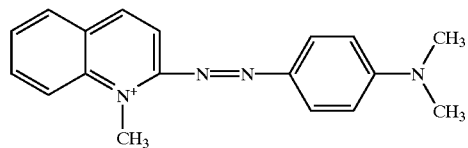
Cl⁻;
(12-3)
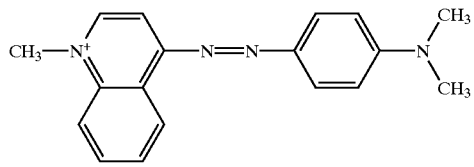
Cl⁻;
(12-4)
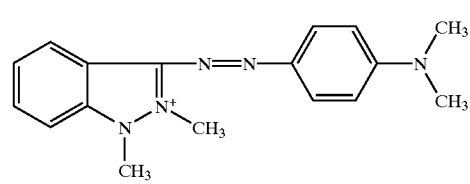
Cl⁻;
(12-5)
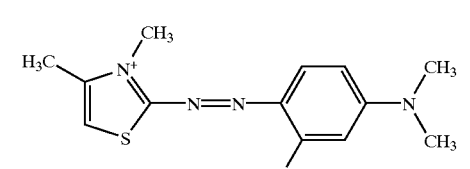
Cl⁻;
(12-6)
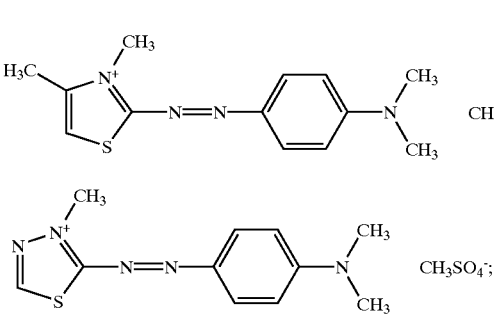
CH₃SO₄⁻;
(12-7)
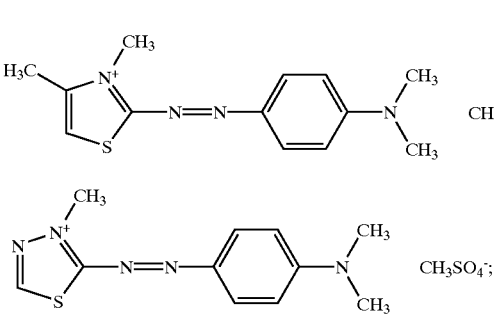
CH₃SO₄⁻;
(12-8)
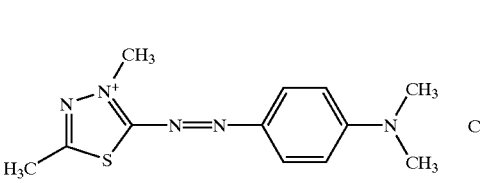
CH₃SO₄⁻;
(12-9)
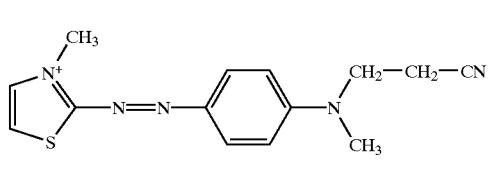
Cl⁻;
(12-10)
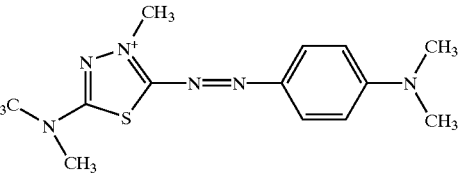
CH₃SO₄⁻;
(12-11)
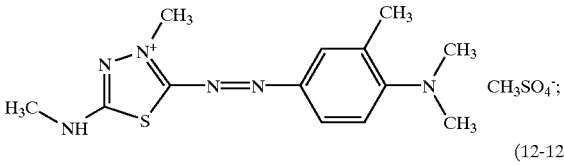
CH₃SO₄⁻;
(12-12)
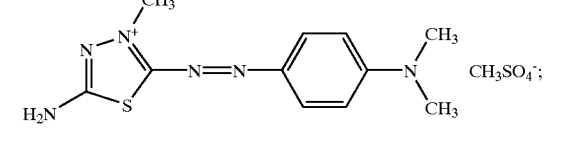
CH₃SO₄⁻;
Those compounds represented by the general formula (13) above as the cationic direct dye that can be added to the composition of the present invention include, for example, those compounds which are represented by the structural formulas (13-1) to (13-18) below.
(13-1)
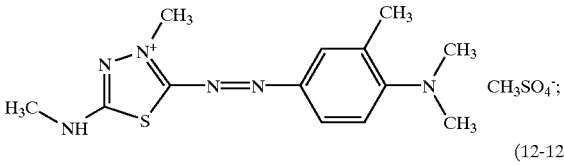
Cl⁻;
(13-2)
Cl⁻;
(13-3)
Cl⁻;
(13-4)
CH₃SO₄⁻;
(13-5)
Cl⁻;
(13-6)
CH₃SO₄⁻;
(13-7)
CH₃SO₄⁻;

Of the compounds represented by the structural formulas (13-1) to (13-18) above, those which are represented by the structural formulas (13-4), (13-5), and (13—13) are particularly preferable.

Those compounds represented by the general formula (13') above as the cationic direct dye that can be added to the composition of the present invention include, for example, those compounds which are represented by the structural formulas (13'-1) to (13'-3) below.

The above-mentioned cationic direct dye should be added in an amount of 0.001 to 10%, preferably 0.05 to 5%, of the total amount of the composition of the present invention.

In general, the acid salts (oxidative base compounds and couplers) which are preferable from the standpoint of the composition of the present invention are hydrochloride, hydrobromide, sulfate, succinate, lactate, and acetate.

A melanin precursor-like substance represented by the formula (14) below is also preferable from the recent nature-loving view point.

X denotes a hydrogen atom, $NH_2$, OH, C1–6 linear or branched alkyl group, alkenyl group, or alkoxyl group; and Y denotes a hydrogen atom, OH, or $NH_2$. If X denotes OH or C1–6 linear or branched alkyl group, alkenyl group, or alkoxyl group, X is at the position 5, 6, or 7 of the ring, and at the ortho position with respect to Y.

Also, $R^{53}$ and $R^{55}$ (which may be identical or different) each denotes a hydrogen atom or C1–6 linear or branched alkyl group, alkenyl group, or alkoxyl group; $R^{54}$ denotes a hydrogen or C1–6 linear or branched alkyl group, alkenyl group, alkoxyl group, or carboxyl group.

Typical examples of the compound represented by the general formula (14) above are listed below:
4,5-dihydroxyindole, 5,6-dihydroxyindole, 6,7-dihydroxyindole, N-methyl-5,6-dihydroxyindole, N-hexyl-5,6-dihydroxyindole, 2-methyl-5,6-dihydroxyindole, 3-methyl-5,6-dihydroxyindole, 4-hydroxyindole, 2,3-dimethyl-5,6-dihydroxyindole, 2-methyl-5-ethyl-6-hydroxindole, 2-methyl-5-hydroxy-6-β-hydroxyethylindole, 4-hydroxypropylindole, 2,3-dimethyl-5,6-dihydroxyindole, 4-hydroxy-5-methoxyindole, 6-hydroxy-7-methoxyindole, 6-hydroxy-5-methoxyindole, 6-hydroxyindole, 5-hydroxyindole, 7-hydroxyindole, 7-aminoindole, 5-aminoindole, 4-aminoindole, 5,6-dihydroxyindole carboxylic acid, 1-methyl-5,6-dihydroxyindole, and salts thereof.

It is also desirable to use the melanin precursor-like substance represented by the general formula (15) below.

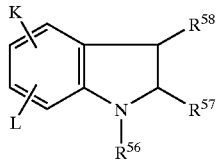

(15)

K denotes a hydrogen atom, $NH_2$, OH, C1–6 linear or branched alkyl group, alkenyl group, or alkoxyl group; and L denotes OH or $NH_2$. If K denotes OH or C1–6 linear or branched alkyl group, alkenyl group, or alkoxyl group, K is at the fifth, sixth, or seventh positions of the ring and at the ortho position with respect to L.

Also, $R^{56}$ and $R^{58}$ (which may be identical or different) each denotes a hydrogen atom or C1–6 linear or branched alkyl group, alkenyl group, or alkoxyl group; $R^{17}$ denotes a hydrogen or C1–6 linear or branched alkyl group, alkenyl group, alkoxyl group, or carboxyl group.

Typical examples of the compound represented by the general formula above are listed below:
4,5-dihydroxyindoline, 5,6-dihydroxyindoline, 6,7-dihydroxyindoline, N-methyl-5,6-dfihydroxyindoline, N-ethyl-5,6-dihydroxyindoline, N-hexyl-5,6-dihydroxyindoline, 2-methyl-5,6-dihydroxyindoline, 3-methyl-5,6-dihydroxyindoline, 4-hydroxyindoline, 2,3-dimethyl-5,6-dihydroxyindoline, 2-methy-5-ethyl-6-hydroxyindoline, 2-methyl-5-hydroxy-6-β-hydroxyethylindoline, 4-hydroxypropylindoline, 2,3-dimethyl-5,6-dihydroxyindoline, 4-hydroxy-5-methoxyindoline, 6-hydroxy-7-methylindoline, 6-hydroxy-5-methoxyindoline, 6-hydroxyindoline, 5-hydroxyindoline, 7-hyroxyindoline, 7-aminoindoline, 5-aminoindoline, 4-aminoindoline, 5,6-dihydroxyindoline carboxylic acid, 1-methyl-5,6-dihydroxyindoline, and salts thereof.

The above-mentioned oxidative color-developing substances may be used alone or in combination with one another for adequate color matching.

The amount of the above-mentioned oxidative color-developing substance in the composition for dyeing keratinous fiber according to the present invention is not specifically restricted. It may be properly increased or reduced for color matching depending on the type of the commodity of the composition and the kind of the oxidative color-developing substance. Usually, it is added in an amount of 0.01 to 20%, preferably 0.1 to 10%, of the total amount of the composition. If the amount of the oxidative color-developing substance is excessive, the amount of the oxidase necessarily decreases to such an extent that it does not produce the oxidizing action, and it is hard to stabilize it. Incidentally, if the amount of the oxidative color-developing substance is too small, the desired effect may not be produced.

The oxidase of the present invention is an oxidase which acts on oxygen as the substrate but does not evolve hydrogen peroxide as mentioned above. A four-electron reductive oxidase is known as such an oxidase, which includes, for example, catechol oxidase, amine oxidase, and laccase. They may be used alone or in combination with one another.

In the composition of the present invention, the amount of the above-mentioned enzyme is not specifically restricted. It varies depending on the type of the product, frequency of use, treatment time, and the potency of the enzyme. For example, it may be used in an amount of 0.01 to 50%, preferably 0.1 to 30%, of the total amount of the composition. If the amount is too small, the above-mentioned oxidase does not fully produce its effect. If the amount is too large, the effect of the oxidase does not increase in proportion to the added amount.

According to the present invention, the amount of the enzyme should preferably be in the above-mentioned range. In the case where the amount of the enzyme is specified, it is desirable to specify the amount on the basis of the active value of the enzyme. It is useful to use the measured value of the amount of dissolved oxygen in the reaction system. The enzyme reaction is a reaction which consumes oxygen in the reaction system and polymerizes the color precursor. It is possible to measure the enzyme activity by monitoring the amount of oxygen consumed.

A commonly used method for determining the amount of dissolved oxygen is the one which uses an oxygen electrode. This method is simple, highly reproducible, and comparatively accurate. In the case of an enzyme reaction system involving a simple combination of oxygen, color-developing oxidative substance, and enzyme, it used to be difficult to obtain constant measured values by measurement with an oxygen electrode; however, it is possible to obtain stable measured values by controlling the temperature for measurement at 0 to 70° C. and by using an adequate buffer solution to adjust the pH value to 6 to 8. In the case where it exists in the form of composition, it is possible to obtain stable measured values by setting up the temperature condition and pH condition in the same way as above although the measurement scale is larger than that in the simple system.

The oxygen electrode as the measuring apparatus is available in three types: oxygen balance type probe, galvanic type probe, and polaragraphic type probe. Any of them gives adequate measured values when used for this object. The enzyme as the active ingredient in the composition to be determined can be determined without restriction of its origin. It should preferably be a four-electron reductive oxidase. Its typical examples include laccase, polyphenol oxidase, and glucose oxidase. To be more specific, they are laccase (E.C. 1.10.3.2), catechol oxidase (E.C. 1.10.3.1), bilirubin oxidase (E.C. 1.3.3.5), and monophenol monooxidase (E.C. 1.14.99.1). Laccase is an enzyme containing a plurality of copper atoms which catalyzes the oxidation of phenols or aromatic amine compounds. The oxidizing reaction by laccase gives rise to aryloxy radials from an adequate phenolic compound. This reaction product yields a dimmer, oligomer, or polymer by polymerization reaction. This laccase originates from microorganisms (such as fungi and bacteria) or plants. Those originating from fungi are preferable. To be more specific, those originating from the following fungi or plants are preferable.
Fungi:
*Polyporus* sp. (e.g., *P. pinsitus* and *P. versicolor*)
*Mycerliophthora* sp. (e.g., *M. thermophila*)
*Phizocutonia* sp. (e.g., *Rh. praticola* and *Rh. solani*)
*Pyriculania* sp. (e.g., *P. oryzae*)
*Scytalidium* sp (e.g., *S. thermophilium*)
Plants:
*Rhus* sp. (e.g., *Rhus vernicifera*)

Among oxidation-reduction enzymes are known the following:
Laccase originating from *Polyporus* sp. (specifically *Polyporus pinisitus*-originating laccase)which laccase is also called *Trametes* Villos-originating laccase disclosed in WO 96/00290 (NOVO Nordisk Biotec Inc.), Laccase originating from *Mytheliophthora thermophila* disclosed in WO 95/33836 (NOVO Nordisk Biotec Inc.), Laccase originating from *Scytalidium* sp. (specifically *S. thermophilium*-originating laccase) disclosed in WO 95/33837 (NOVO Nordisk Biotec Inc.). Included in them are laccase originating from *Pyriculania* sp. (*Pyricularia oryzae*) which is commercially available from SIGMA Corp. under a trade name of L5510, laccase originating from *Coprinus* sp. (*C. Cinereus*), and laccase originating from *Rhizoctonia* sp. (*Rh. solani*) with an optimum pH 6.0–8.5 disclosed in WO 95/07988.

Other known laccases are those originating from the following fungi: *Collybia, Fomes, Letium, Pleurotus, Aspergillus, Neutospora, Podospora, Phlebia* (*P. radiata*) disclosed in WO 92/0104, *Coriolus* sp. (*C. hirsitus*) disclosed in JP 2-238885, and *Botrytis*.

A preferred bilirubin oxidase is the one originating from *Mycrothecim* sp. (*M. verrucaria*).

The $H_2O_2$-producing oxidase is usually used in combination with a peroxide which decomposes $H_2O$ or decreases the production of $H_2O_2$. Such a peroxidase includes, for example, glucose oxidase (E.C. 1.1.3.4), hexose oxidase (E.C. 1.1.3.5), L-amino acid oxidase (E.C. 1.4.3.2), xylitol oxidase, galactose oxidase (E.C. 1.1.3.9), pyranose oxidase (E.C. 1.1.3.10), and alcohol oxidase (E.C. 1.1.3.13).

The L-amino acid oxidase should preferably be the one which originates from *Trichloderma* sp. (specifically *T. harzianum*) disclosed in WO 94/25574 NOVO Nordisk A/S, or the one which originates from *T. viride*.

The glucose oxidase should preferably be one which originates from *Aspergillus* sp. (*A. niger*) or *Cladosporium* sp. (specifically *C. oxysprorum*).

The hexose oxidase is an enzyme which oxidizes carbohydrates such as D-glucose, D-galactose, maltose, cellobiose, lactose, D-glucose-6-phosphate, D-mannose, 2-deoxy-D-glucose, 2-doxy-D-galactose, D-fructose, D-glucuronic acid, and D-xylose, which originate from Chondrus. Crispus (known as Irish moss) as red algae. (Sullivan and Ikawa, (1973), Biochim. Biophys. Acts, 309, p. 11–22; Ikawa, (1982), Meth. in Enzymol. 89, Carbohydrate Metabolism Part D, 145–149)

The measuring method mentioned herein can be applied to them regardless of their origin. In the composition of the present invention, the amount of the oxidase should be 0.005–10.0, preferably 0.01–5.0, in terms of active ingredient (ΔDO value) specified by the measuring method. This amount is adequate for good dyeing property. The oxidase regardless of its origin can be used in the composition of the present invention. More than one oxidase may be used in combination with one another.

The measurement of activity employs as the substrate color-developing substances such as dye precursor, developer, and direct dye. Their kind and amount are not specified for color matching. Ordinary oxidation dyes mentioned above can be used, which include the one mentioned in the standard for hair dye raw materials (The $3^{rd}$ revised edition, issued in May 1985, by Japan Hair Color Industry Association, Hair Dye Forum).

The practical method for determination is explained in the following:
(1) Method for Determination
(Apparatus)
Dissolved oxygen meter, thermostat, incubator (102 mL), beaker (made of glass), magnetic stirrer, stirrer bar, clamp, timer, and measuring flask.

| | (Substrates for measurment) | | | | | | | | | |
|---|---|---|---|---|---|---|---|---|---|---|
| | (a) | (b) | (c) | (d)* | (e)* | (f) | (g) | (h) | (i)* | (j)* |
| p-aminophenol | 2 | 0.2 | 0.8 | 1 | | 0.5 | 0.5 | 0.5 | 0.5 | |
| p-phenylenediamine | | 0.4 | | 0.2 | | 1 | | 1 | 1 | |
| m-phenylenediamine | | 1 | | 0.2 | | 0.5 | 0.5 | 0.5 | 0.5 | |
| m-aminophenol | | | 0.6 | 0.4 | | | 0.5 | 0.05 | 0.05 | |
| m-diphenol | | | 0.4 | 0.04 | | | | 0.15 | 0.15 | |
| o-aminocresol | | | | | | | 0.05 | | | |
| Resorcin | | | | | | | 0.1 | | | |
| 2,5-diaminotoluene sulfate | | | | | | 2 | 2 | 2 | 2 | |
| 2-(2'-hydroxyethyl-amino)-5-aminotoluene sulfate | | | | | | 0.15 | | | | |
| Polymeric thickener | | | | | | 0.5 | 0.05 | 1.5 | 1.5 | 1.5 |
| pH adjustor | | | | | | 2 | 1 | 0.2 | 0.2 | 0.2 |
| Antioxidant | | | | | | 2 | 2.5 | 2 | 2 | 2 |
| Dispersing and emulsifying agent | | | | | | 1 | 1.5 | 1 | 1 | 1 |
| Oil | | | | | | 0.2 | 0.15 | 0.2 | 0.2 | 0.2 |
| Permeation auxiliary | | | | | | 0.2 | 0.3 | 0.2 | 0.2 | 0.2 |

-continued

| | (Substrates for measurment) | | | | | | | | | |
|---|---|---|---|---|---|---|---|---|---|---|
| | (a) | (b) | (c) | (d)* | (e)* | (f) | (g) | (h) | (i)* | (j)* |
| Enzyme | Laccase | Laccase | Laccase | Uricase | Laccase 0.02 | Laccase | Laccase | Laccase | Uricase | Laccase 1 |
| Uric acid | | | | | | | | | | |
| 50 mM boric acid-potassium hydroxide buffer (pH 8.5) | | | | Balance | Balance | | | | | |
| Ethanol | 96 | 96 | 96 | 96 | | 10 | 5 | 10 | 10 | 10 |
| Purified water | Balance | Balance | Balance | | | Balance | Balance | Balance | Balance | Balance |

Asterisk (*) indicates comparison.
Total amount is 100 mass %.

(Method 1)
(1) Place the buffer solution for measurement in the incubator or beaker, and keep it warm.
(2) Add the substrate for measurement to the buffer solution, and uniformly mix the solution with the stirrer.
(3) Insert the oxygen electrode and mix the solution with the stirrer to stabilize the system.
(4) Add the enzyme sample and start the timer simultaneously.
(5) Determine the amount of dissolved oxygen at a certain interval, and record the difference (ΔDO) of two measurements.

(Method 2)
(1) Place the buffer solution for measurement in the incubator or beaker, and keep it warm.
(2) Add the enzyme sample to the buffer solution, and uniformly mix the solution with the stirrer.
(3) Insert the oxygen electrode and mix the solution with the stirrer to stabilize the system.
(4) Add the substrate for measurement and start the timer simultaneously.
(5) Determine the amount of dissolved oxygen at a certain interval, and record the difference (ΔDO) of two measurements.

(Method 3)
(1) Place a predetermined amount the composition sample (containing the enzyme) in the incubator or beaker.
(2) Add the buffer solution (previously warmed) and run the stirrer.
(3) Insert the oxygen electrode and start the timer.
(4) Determine the amount of dissolved oxygen at a certain interval, and record the difference (ΔDO) of two measurements.

(Results)

The method 1 or 2 was used for the substrates (a) to (e), the method 3 was used for the substrates (f) to (j). The results of determination are shown in Table 1 below.

It is noted that the value of ΔDO changes as the amount of the enzyme added (or in the composition) increases. This suggests that the above-mentioned method is suitable for determining the amount of the enzyme as the active ingredient in the composition. It is also noted from the results of comparative example that uric acid is inadequate as the reaction substrate and it is impossible to determine the activity of the enzyme by using uric acid.

TABLE 1

| | Measured values (ΔDO values) | | | | | | | | | | | | | | | |
|---|---|---|---|---|---|---|---|---|---|---|---|---|---|---|---|---|
| Amount of Enzyme (wt %) | 0 | 1 | 2 | 3 | 4 | 5 | 6 | 7 | 8 | 9 | 10 | 11 | 12 | 13 | 14 | 15 |
| (a) | 0 | 0.1 | 0.3 | 0.45 | 0.6 | 0.8 | 0.9 | 1.1 | 1.2 | 1.35 | 1.56 | 1.87 | 2.1 | 2.4 | 2.75 | 3 |
| (b) | 0 | 0.005 | 0.2 | 0.4 | 0.8 | 1.5 | 2.2 | 2.8 | 3.5 | 4.1 | 4.7 | 5.3 | 5.8 | 6.4 | 6.9 | 7.5 |
| (c) | 0 | 0.03 | 0.3 | 0.6 | 1.1 | 1.7 | 2.2 | 3.4 | 4.2 | 5 | 6.3 | 7.1 | 7.9 | 8.8 | 9.3 | 10.2 |
| (d) comparison | 0 | 0 | 0 | 0 | 0 | 0 | 0 | 0 | 0 | 0 | 0 | 0 | 0 | 0 | 0 | 0 |
| (e) comparison | 0 | 0 | 0 | 0 | 0 | 0 | 0 | 0 | 0 | 0 | 0 | 0 | 0 | 0 | 0 | 0 |
| (f) | 0 | 0.1 | 0.23 | 0.4 | 0.5 | 0.63 | 0.83 | 1 | 1.25 | 1.6 | 1.9 | 2.3 | 2.6 | 3 | 3.3 | 3.5 |
| (g) | 0 | 0.1 | 0.3 | 0.5 | 0.75 | 1.1 | 1.4 | 1.9 | 2.2 | 2.6 | 2.9 | 3.2 | 3.5 | 4 | 4.5 | 5 |
| (h) | 0 | 0.5 | 0.9 | 1.5 | 2.2 | 3 | 3.6 | 4.3 | 4.8 | 5.5 | 6 | 6.8 | 7.4 | 8 | 9 | 10 |
| (i) comparison | 0 | 0 | 0 | 0 | 0 | 0 | 0 | 0 | 0 | 0 | 0 | 0 | 0 | 0 | 0 | 0 |
| (j) comparison | 0 | 0 | 0 | 0 | 0 | 0 | 0 | 0 | 0 | 0 | 0 | 0 | 0 | 0 | 0 | 0 |

The weak reducing agent used in the present invention implies any reducing agent whose pseudo first-order reaction rate constant $K_{obs}$ (as an index of reducing capacity) is smaller than 0.001 s$^{-1}$ (measured by the following method).

<Method for Measurement of Pseudo First-Order Reaction Rate Constant $K_{obs}$>

A solution is prepared which contains 300 mM of the reducing agent to be measured and 100 mM of phosphate buffer (pH=5). To this solution is added a legal dye (violet No. 401) in an amount of 0.2 mM. The resulting solution is measured for the change of peak with time at the wavelength of 575 nm by using a UV meter (Model UV-160 made by Shimadzu Corporation). The rate constant for change with time is obtained, and it is defined as the pseudo first-order reaction rate constant $K_{obs}$.

The above-mentioned weak reducing agent includes, for example, sodium thiosulfate, dl-cysteine, N-acetyl-L-cysteine, thiourea, dithioglycolic acid, L-ascorbic acid, sorbic acid, adipic acid, and salts thereof. They may be used alone or in combination with one another. The value of $K_{obs}$ obtained by the above-mentioned method is as follows:
0.0081 for thioglycolic acid and 0.0068 for sodium sulfite (as strong reducing agents)
0.00075 for sodium thiosulfate, 0.00031 for N-acetyl-L-cysteine, and 0.00045 for thiourea (as weak reducing agents mentioned above)

The amount of the above-mentioned weak reducing agent in the composition is not specifically restricted; it may be adequately selected according to the kind of the weak reducing agent. It is usually equal to or less than 10%, preferably 0.01 to 10%, more preferably 0.1 to 7%. An excess amount may adversely affect dyeing power on account of excessively strong reducing action. The desired effect may not be produced if the amount is too small.

The composition of the present invention may be effective if containing cyclodextrin in addition to the above-mentioned essential ingredients. The cyclodextrin includes cyclodextrin and derivatives thereof. Cyclodextrin is a non-reducing maltoligosaccharide which has the structure in which 6 to 8 glucose molecules are connected to form a ring through the α-1,4-glucoside bond. It takes the α-form, β-form, or γ-form depending on the number of glucose molecules connected together. The especially effective cyclodextrin derivative is one which is obtained by adding propylene oxide to said cyclodextrin. The number of moles to be added is not specifically restricted. It is usually 3 to 8 for one molecule. More than one kind of cyclodextrin may be used according to the compound to be included.

The amount of the above-mentioned cyclodextrin in the composition is not specifically restricted; it is usually 0.1 to 75%, preferably 0.5 to 60%. Cyclodextrin does not fully produce its effect if its amount is too small, and it does not produce its effect in proportion to its amount if its amount is too large.

The composition for dyeing keratinous fiber according to the present invention may be incorporated with additional components as listed below according to need so long as they do not prevent the effect of the present invention.

Acid, alkali as pH adjustor, surface active agent, ionic or nonionic natural or synthetic or semisynthetic polymeric compound, ester oil, vegetable oil, silicone derivative, fluorine derivative, amino acid, salts, alcohol (as solvent), dandruff remover, chelating agent, preservatives, UV absorber, fungicide, antioxidant, perfume, acid dye, and natural dye. These components are conventionally used ones, and they are added in an ordinary amount not harmful to the effect of the present invention.

The composition for dyeing keratinous fiber according to the present invention can be prepared in one-pack form by mixing the above-mentioned components in the usual way for dissolution, dispersion, or emulsification. A liquid solution type is desirable; but other types are also available such as paste (cream), aerosol, gel, liquid, and foam. The resulting preparations can be applied to hair, eyebrow, eyelash, and body hair to dye them as desired.

The invention will be described in more detail with reference to the following examples and comparative examples, which are not intended to restrict the scope of the invention.

EXAMPLES 1 TO 12 AND COMPARATIVE EXAMPLES 1 TO 6

A stock solution for hair dye was prepared by uniformly mixing in the usual way with the components shown in Tables 2 and 3. The stock solution was placed in a glass pressure bottle, which was subsequently clinched under vacuum. The bottle was charged with LPG (2.0 kg) as a propellant in such an amount that the ratio of stock solution to gas is 95:5 (by mass). In this way there were obtained aerosol-type hair dyes (compositions for dyeing keratinous fiber) in Examples 1 to 12 and Comparative Examples 1 to 6. Each sample was examined for storage stability and dyeing property. The results are shown in Table 2 and 3.

(Test for Storage Stability)

Each sample was stored for six months at room temperature and for one month at 45° C. After storage, each sample was visually examined for aggregates, precipitates, and discoloration, and the results were rated according to the following criterion.

Rating Criterion

◎: Aggregates, precipitates, and discoloration not discernible

○: Aggregates, precipitates, and discoloration slightly discernible

Δ: Aggregates, precipitates, and discoloration apparently discernible

×: Not usable due to excessive aggregates, precipitates, and discoloration

<Test for Hair Dyeing>

A bundle of goat white hair (about 10 g) was shampooed and dried. This hair was uniformly and rapidly coated with each sample (3 g) shown in Tables 2 and 3. After standing for about 20 minutes, the bundle of dyed hair was rinsed with running warm water and then shampooed and dried. The bundle of dried hair was measured for hair dyeing index (ΔE) by using a color difference meter (SE 2000 made by Nippon Denshoku Co., Ltd.) The hair dyeing index (ΔE) is obtained by measurement of L, a, b values of the dyed hair and calculating color difference (ΔE) from the undyed hair. This measurement was carried out immediately after preparation and after storage under the prescribed conditions mentioned above, so as to investigate the effect of storage. The larger the value of ΔE, the better the dyeing property.

TABLE 2

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Composition | Toluene-2,5-diamine sulfate | 2.0 | 2.0 | | | 1.5 | 1.5 | 2.0 | 2.0 | 2.0 | 2.0 | 2.0 | 2.0 |
| | p-phenylenediamine | | | 1.5 | 1.5 | 0.5 | 0.5 | 1.5 | 1.5 | | | | |
| | Resorcin | 0.5 | 0.5 | 0.75 | 0.75 | 0.25 | 0.25 | | | 1.5 | 1.5 | | |
| | Nitro-p- | 1.0 | 1.0 | | | 0.1 | 0.1 | | | | | | |

TABLE 2-continued

|  |  | Examples | | | | | | | | | | | |
|---|---|---|---|---|---|---|---|---|---|---|---|---|---|
|  |  | 1 | 2 | 3 | 4 | 5 | 6 | 7 | 8 | 9 | 10 | 11 | 12 |
|  | phenylenediamine p-nitro-o-phenylenediamine |  |  |  |  |  |  |  |  |  |  | 1.5 | 1.5 |
|  | 2,6-diaminopyridine |  |  | 2.0 | 2.0 | 0.3 | 0.3 | 1.0 | 1.0 | 0.75 | 0.75 | 0.5 | 0.5 |
|  | Lauric acid | 0.3 | 0.3 | 0.3 | 0.3 | 0.3 | 0.3 | 0.3 | 0.3 | 0.3 | 0.3 | 0.3 | 0.3 |
|  | Coconut oil fatty acid diethanolamine | 1.0 | 1.0 | 1.0 | 1.0 | 1.0 | 1.0 | 1.0 | 1.0 | 1.0 | 1.0 | 1.0 | 1.0 |
|  | Sorbitan laurate | 0.5 | 0.5 | 0.5 | 0.5 | 0.5 | 0.5 | 0.5 | 0.5 | 0.5 | 0.5 | 0.5 | 0.5 |
|  | Ethanol | 10 | 10 | 10 | 10 | 10 | 10 | 10 | 10 | 10 | 10 | 10 | 10 |
|  | Hydroxyethylcellulose | 2.5 | 2.5 | 2.5 | 2.5 | 2.5 | 2.5 | 2.5 | 2.5 | 2.5 | 2.5 | 2.5 | 2.5 |
|  | Lactic acid | 0.2 | 0.2 | 0.2 | 0.2 | 0.2 | 0.2 | 0.2 | 0.2 | 0.2 | 0.2 | 0.2 | 0.2 |
|  | β-cyclodextrin |  | 1.0 |  | 1.0 |  | 1.2 |  | 1.0 |  | 1.5 |  | 1.0 |
|  | Laccase[3] | $7.0^1$ | $7.0^1$ | $7.0^1$ | $7.0^1$ |  |  |  | $3.5^2$ | $3.5^2$ |  | $7.0^1$ | $7.0^1$ |
|  | Catechol oxidase[4] |  |  |  |  | $7.0^1$ | $7.0^1$ | $3.5^2$ | $3.5^2$ | $7.0^1$ | $7.0^1$ |  |  |
|  | N-acetyl-L-cysteine | 1.0 | 1.0 | 1.0 | 1.0 | 1.0 | 1.0 |  |  | 1.0 | 1.0 |  |  |
|  | Thiourea |  |  |  |  |  |  | 0.3 | 0.3 |  |  | 0.3 | 0.3 |
|  | Monoethanolamine | Enough to adjust to pH 7.0 | | | | | | | | | | | |
|  | Purified water | Balance | | | | | | | | | | | |
|  | Total (mass %) | 100.0 | | | | | | | | | | | |
| Appearance, Storage stability | Initial | ⊚ | ⊚ | ⊚ | ⊚ | ⊚ | ⊚ | ⊚ | ⊚ | ⊚ | ⊚ | ⊚ | ⊚ |
|  | After storage for 6 months at r.t. | ⊚-○ | ⊚ | ⊚-○ | ⊚ | ⊚-○ | ⊚ | ⊚-○ | ⊚ | ⊚-○ | ⊚ | ⊚-○ | ⊚ |
|  | After storage for 1 month at 45° C. | ⊚-○ | ⊚ | ⊚-○ | ⊚ | ⊚-○ | ⊚ | ⊚-○ | ⊚ | ⊚-○ | ⊚ | ⊚-○ | ⊚ |
| Discoloration, Storage Stability | Initial (initial color) | ⊚ (r) | ⊚ (r) | ⊚ (lb) | ⊚ (lb) | ⊚ (rb) | ⊚ (rb) | ⊚ (ly) | ⊚ (ly) | ⊚ (lb) | ⊚ (lb) | ⊚ (dy) | ⊚ (dy) |
|  | After storage for 6 months at r.t. | ⊚-○ | ⊚ | ⊚-○ | ⊚ | ⊚-○ | ⊚ | ⊚-○ | ⊚ | ⊚-○ | ⊚ | ⊚-○ | ⊚ |
|  | After storage for 1 month at 45° C. | ⊚-○ | ⊚ | ⊚-○ | ⊚ | ⊚-○ | ⊚ | ⊚-○ | ⊚ | ⊚-○ | ⊚ | ⊚-○ | ⊚ |
| Dyeing Property, ΔE | Dyed color | lb | lb | nb | nb | db | db | bk | bk | bk | bk | y | y |
|  | Initial | 31.0 | 31.5 | 30.2 | 30.9 | 32.1 | 32.0 | 35.5 | 35.0 | 33.1 | 33.5 | 28.8 | 28.5 |
|  | After storage for 1 month at 45° C. | 30.1 | 30.8 | 29.7 | 29.8 | 30.2 | 30.4 | 32.1 | 32.3 | 30.0 | 30.3 | 27.4 | 27.4 |

Note to Table 2
$7.0^1$: equivalent to ΔDO = 1.0
$3.5^2$: equivalent to --ΔDO = 0.5
Laccase[3]: with an active value equivalent to ΔDO = 15.3
Catechol oxidase[4]: with an active value equivalent to ΔDO = 15.5
Color: r = red, lb = light brown, ly = light yellow, dy = dark yellow, nb = navy blue, db = dark brown, bk = black, y = yellow.
r.t. = room temperature

TABLE 3

|  |  | Comparative Examples | | | | | |
|---|---|---|---|---|---|---|---|
|  |  | 1 | 2 | 3 | 4 | 5 | 6 |
| Composition | Toluene-2,5-diamine sulfate | 2.0 | 2.0 | 2.0 | 2.0 | 2.0 | 2.0 |
|  | p-phenylenediamine |  |  |  |  |  |  |
|  | Resorcin | 0.5 | 0.5 | 0.5 | 0.5 | 0.5 | 0.5 |
|  | Nitro-p-phenylenediamine |  |  |  |  |  |  |
|  | p-nitro-o-phenylenediamine |  |  |  |  |  |  |
|  | 2,6-diaminopyridine | 1.0 | 1.0 | 1.0 | 1.0 | 1.0 | 1.0 |
|  | Lauric acid | 0.3 | 0.3 | 0.3 | 0.3 | 0.3 | 0.3 |
|  | Coconut oil fatty acid diethanolamine | 1.0 | 1.0 | 1.0 | 1.0 | 1.0 | 1.0 |
|  | Sorbitan laurate | 0.5 | 0.5 | 0.5 | 0.5 | 0.5 | 0.5 |
|  | Ethanol | 10 | 10 | 10 | 10 | 10 | 10 |
|  | Hydroxyethylcellulose | 2.5 | 2.5 | 2.5 | 2.5 | 2.5 | 2.5 |
|  | Lactic acid | 0.2 | 0.2 | 0.2 | 0.2 | 0.2 | 0.2 |

TABLE 3-continued

| | | Comparative Examples | | | | | |
|---|---|---|---|---|---|---|---|
| | | 1 | 2 | 3 | 4 | 5 | 6 |
| | β-cyclodextrin | | 1.0 | | | 1.0 | 1.0 |
| | Laccase[(3)] | | | | 7.0[1] | | 7.0[1] |
| | Catechol oxidase | | | | | | |
| | N-acetyl-L-cysteine | | | 1.0 | | 1.0 | |
| | Thiourea | | | | | | |
| | Monoethanolamine | Enough to adjust to pH 7.0 | | | | | |
| | Purified water | Balance | | | | | |
| | Total (mass %) | 100.0 | | | | | |
| Appearance, Storage stability | Initial | ◎ | ◎ | ◎ | ◎ | ◎ | ◎ |
| | After storage for 6 months at r.t. | ◎ | ◎ | ○ | × | ◎ | ◎ |
| | After storage for 1 months at 45° C. | ◎ | ◎ | ◎ | × | ◎ | ◎ |
| Discoloration, Storage Stability | Initial (initial color) | ◎(ly) | ◎(ly) | ◎(ly) | ◎(ly) | ◎(ly) | ◎(ly) |
| | After storage for 6 months at r.t. | ○ | ○ | ○ | × | ◎ | Δ |
| | After storage for 1 month at 45° C. | ◎ | ◎ | ◎ | × | ◎ | × |
| Dyeing Property, ΔE | Dyed color | not dyed | not dyed | not dyed | lb | not dyed | lb |
| | Initial | 5.4 | 6.6 | 5.0 | 29.9 | 4.5 | 29.5 |
| | After storage for 1 month at 45° C. | 3.2 | 4.2 | 3.8 | 8.4 | 3.2 | 21.8 |

Note to Table 3.
7.0[1]: equivalent to ΔDO = 1.0
Laccase[(3)]: with an active value equivalent to ΔDO = 15.3
Color: ly: light yellow, lb: light brown
r.t. = room temperature It is noted from Tables 2 and 3 that the composition for dyeing keratinous fiber (reactive hair dye) according to the present invention exhibits very good storage stability and dyeing property. It exhibits better stability and dyeing property if it is additionally incorporated with β-cyclodextrin. By contrast, the samples in Comparative Examples 1, 2, 3, and 5, which do not contain the oxidase specified in the present invention, are stable but incapable of dyeing because of the lack of oxidizing ability. The samples in Comparative Examples 4 and 6, which do not contain the weak reducing agent specified in the present invention, are capable of dyeing immediately after preparation but deteriorate with aggregates, precipitates, and discoloration after storage for six months at room temperature or for one month at 45° C. They are also poor in dyeing property.

Specific examples of the composition are shown below, although they are not intended to restrict the scope of the present invention. The laccase used in the following examples is one which has an active value equivalent to ΔDO=15.3.

EXAMPLE 13

One-Pack Hair Dye (in the Form of Foam)

| Components (Stock solution) | Amount (mass %) |
|---|---|
| p-phenylenediamine | 1.0 |
| 2,5-diaminotoluene sulfate | 2.0 |
| m-phenylenediamine | 0.5 |
| p-aminophenol | 0.5 |
| 2-(2'-hydroxyethylamino)-5-aminotoluene sulfate | 0.15 |
| Oleic acid | 0.2 |
| Oleyl alcohol | 0.2 |
| β-cyclodextrin | 1.0 |
| Laccase | 7.0[(1)] |
| Sodium polyacrylate (cross-linked type) | 1.0 |
| Cationized hydroxyethyl cellulose | 0.5 |
| N-acetyl-L-cysteine | 1.0 |
| Sorbitan monolaurate | 1.0 |
| Ethanol | 10.0 |
| Glycolic acid | 0.2 |
| Perfume | 0.1 |
| Purified water | balance |
| (Adjusted to pH 6.5 with monoethanolamine) | |
| Total | 100 |

Laccase 7.0[(1)]: equivalent to ΔDO = 1.0

A stock solution was prepared in the usual way according to the above-mentioned formulation. The stock solution was placed in an aerosol can, which was subsequently clinched under vacuum. The aerosol can was filled with LPG (2.0 kg) as a propellant such that the ratio of stock solution to gas is 95:5 (by mass). Thus there was obtained a hair dye of aerosol type. The LPG as a compressed gas may be replaced by any one or more of nitrogen, carbon dioxide gas, dinitrogen monoxide gas, flon 11, flon 12, and flon 114. The aerosol type may be direct spray type or piston type in an aluminum can or tinplate can, or the aerosol can may be double-walled can such as back-in type and EXXEL type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in blue black. This color was the same as that obtained when the hair dye was used immediately after production.

EXAMPLE 14

One-Pack Hair Dye (in the Form of Foam)

| Components (Stock solution) | Amount (mass %) |
|---|---|
| 5,6-dihydroxyindoline hydrobromide | 1.0 |
| 5,6-dihydroxyindole hydrochloride | 1.0 |
| N-ethyl-5,6-dihydroxyindole hydrochloride | 0.05 |
| Linoleic acid | 0.2 |
| Oleyl alcohol | 0.2 |
| β-cyclodextrin | 1.0 |
| Laccase | 7.0[(1)] |
| Hydroxyethyl cellulose | 0.5 |
| Coconut oil fatty acid sodium acyl-glutamate | 1.0 |
| N-acetyl-L-cysteine | 0.5 |
| Thiourea | 0.3 |
| Sodium polyacrylate (cross-linked type) | 0.2 |
| Ethanol | 10.0 |
| Lactic acid | 0.2 |
| Perfume | 0.1 |
| Purified water | balance |
| (Adjusted to pH 6.8 with monoethanolamine) | |
| Total | 100 |

Laccase 7.0[(1)]: equivalent to ΔDO = 1.0

A stock solution was prepared in the usual way according to the above-mentioned formulation. The stock solution was placed in an aerosol can, which was subsequently clinched under vacuum. The aerosol can was filled with LPG (2.0 kg) as a propellant such that the ratio of stock solution to gas is 95:5 (by mass). Thus there was obtained a hair dye of aerosol type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in black. This color was the same as that obtained when the hair dye was used immediately after production.

EXAMPLE 15

One-Pack Hair Dye (in the Form of Creamy Foam)

| Components (Stock solution) | Amount (mass %) |
|---|---|
| 2,5-diaminotoluene sulfate | 2.0 |
| m-phenylenediamine | 0.5 |
| m-aminophenol | 0.5 |
| Resorcin | 0.1 |
| o-aminocresol | 0.05 |
| Oleic acid | 0.2 |
| β-cyclodextrin | 1.2 |
| Laccase | 10.5[(2)] |
| Xanthan gum | 0.05 |
| Sodium sulfite | 0.05 |
| Thiourea | 0.05 |
| N-acetyl-L-cysteine | 0.5 |
| Stearyl trimethylammonium chloride | 0.2 |
| Cetostearyl alcohol | 0.6 |
| POE (20) hardened castor oil triisostearate | 0.2 |
| Sorbitan monostearate | 0.1 |
| Methylparaben | 0.3 |
| Glycolic acid | 0.2 |
| Propylene glycol | 5.0 |
| Perfume | 0.1 |
| Purified water | balance |
| (Adjusted to pH 7.0 with monoethanolamine) | |
| Total | 100 |

Laccase 10.5[(2)]: equivalent to ΔDO = 1.5

A stock solution was prepared in the usual way according to the above-mentioned formulation. The stock solution was placed in an aerosol can, which was subsequently clinched under vacuum. The aerosol can was filled with LPG (4.0 kg) as a propellant such that the ratio of stock solution to gas is 95:5 (by mass). Thus there was obtained a creamy hair dye of aerosol type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in dark brown. This color was the same as that obtained when the hair dye was used immediately after production.

EXAMPLE 16

One-Pack Hair Dye (in the Form of Creamy Foam)

| Components (Stock solution) | Amount (mass %) |
|---|---|
| 5,6-dihydroxyindoline hydrobromide | 1.0 |
| 5,6-dihydroxyindole hydrochloride | 1.0 |
| N-methyl-5,6-dihydroxyindole hydrobromide | 0.05 |
| Linoleic acid | 0.2 |
| β-cyclodextrin | 1.0 |
| Laccase | 10.5[(2)] |
| Sodium sulfite | 0.09 |
| N-acetyl-L-cysteine | 0.3 |
| Cetostearyl trimethylammonium chloride | 0.2 |
| Cetostearyl alcohol | 0.6 |
| POE (20) hardened castor oil monoisostearate | 0.2 |
| Sorbitan monostearate | 0.1 |
| Methylparaben | 0.3 |
| Lactic acid | 0.2 |
| Diethylene glycol monoethyl ether | 5.0 |
| 1,3-butylene glycol | 3.0 |
| Perfume | 0.1 |
| Purified water | balance |
| (Adjusted to pH 7.0 with monoethanolamine) | |
| Total | 100 |

Laccase 10.5[(2)]: equivalent to ΔDO = 1.5

A stock solution was prepared in the usual way according to the above-mentioned formulation. The stock solution was placed in an aerosol can, which was subsequently clinched under vacuum. The aerosol can was filled with LPG (4.0 kg) as a propellant such that the ratio of stock solution to gas is 95:5 (by mass). Thus there was obtained a hair dye of aerosol type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in black. This color was the same as that obtained when the hair dye was used immediately after production.

EXAMPLE 17

One-Pack Hair Dye (Cream Type)

| Components | Amount (mass %) |
|---|---|
| 5,6-dihydroxyindoline hydrobromide | 1.0 |
| 5,6-dihydroxyindole hydrochloride | 1.0 |
| N-methyl-5,6-dihydroxyindole hydrobromide | 0.05 |
| N-methyl-5,6-dihydroxyindole hydrochloride | 0.05 |
| 2,5-diaminotoluene sulfate | 0.01 |
| β-cyclodextrin | 1.0 |
| Laccase | 14.0[3] |
| N-acetyl-L-cysteine | 0.5 |
| Thiourea | 0.3 |
| Alkyl trimethylammonium chloride | 0.5 |
| Coconut oil fatty acid acyl-L-arginine ethyl-D,L-pyrrolidone carboxylate | 0.5 |
| Cetostearyl alcohol | 2.0 |
| Oleyl alcohol | 1.0 |
| POE (40) hardened castor oil | 0.75 |
| POE (20) stearyl ether | 0.75 |
| Sorbitan sesquistearate | 1.0 |
| Methylparaben | 0.3 |
| Propylene glycol | 5.0 |
| Glycolic acid | 0.2 |
| Perfume | 0.1 |
| Purified water | balance |
| (Adjusted to pH 7.5 with monoethanolamine) | |
| Total | 100 |

Laccase 14.0[3]: equivalent to ΔDO = 2.0

The above-mentioned components were uniformly mixed in the usual way to give a hair dye of cream type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in dark brown. This color was the same as that obtained when the hair dye was used immediately after production.

EXAMPLE 18

One-Pack Hair Dye (Cream Type)

| Components | Amount (mass %) |
|---|---|
| 2,5-diaminotoluene sulfate | 2.0 |
| 2,6-diaminopyridine | 0.05 |
| N,N-bis(β-hydroxyl)-p-phenylenediamine | 0.1 |
| 2-amino-5-orthophenol | 0.5 |
| 2-(2'-hydroxyethylamino)-5-aminotoluene | 0.15 |
| Linoleic acid | 0.2 |
| β-cyclodextrin | 1.0 |
| Laccase | 14.0[3] |
| N-acetyl-L-cysteine | 1.0 |
| Thiourea | 0.5 |
| Stearyl trimethylammonium chloride | 0.5 |
| Behenyl trimethylammonium chloride | 0.5 |
| Cetostearyl alcohol | 2.0 |
| Oleyl alcohol | 1.0 |
| POE (40) glycerin triisostearate | 0.75 |
| POE (20) lauryl ether | 0.75 |
| Sorbitan monostearate | 1.0 |
| Methylparaben | 0.3 |
| Propylene glycol | 5.0 |
| Lactic acid | 0.2 |
| Perfume | 0.1 |
| Purified water | balance |
| (Adjusted to pH 7.0 with monoethanolamine) | |
| Total | 100.0 |

Laccase 14.0[3]: equivalent to ΔDO = 2.0

The above-mentioned components were uniformly mixed in the usual way to give a hair dye of cream type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in light brown. This color was the same as that obtained when the hair dye was used immediately after production.

EXAMPLE 19

One-Pack Hair Dye (Treatment Type)

| Components | Amount (mass %) |
|---|---|
| 2,5-diaminotoluene sulfate | 5.0 |
| 2-amino-4-nitrophenol | 3.0 |
| 5-amino-o-cresol | 1.0 |
| p-aminophenol | 1.0 |
| Oleic acid | 0.5 |
| Linoleic acid | 0.5 |
| β-cyclodextrin | 2.0 |
| Laccase | 14.0[3] |
| N-acetyl-L-cysteine | 1.0 |
| Thiourea | 0.5 |
| Stearyl trimethylammonium chloride | 0.5 |
| Cetyl trimethylammonium chloride | 0.5 |
| Cetostearyl alcohol | 4.0 |
| Oleyl alcohol | 1.0 |
| Ethyl oleate | 0.5 |
| Isopropyl palmitate | 0.5 |
| Liquid paraffin | 1.0 |
| Beeswax | 0.5 |
| POE (40) hardened castor oil triisostearate | 0.25 |
| POE (20) hardened castor oil triisostearate | 0.25 |
| POE (30) stearyl ether | 0.75 |
| Sorbitan monostearate | 1.0 |
| Glycerin monostearate | 0.5 |
| Methylparaben | 0.3 |
| Propylene glycol | 5.0 |
| Glycerin | 3.0 |
| Glycolic acid | 0.2 |
| Perfume | 0.1 |
| Purified water | balance |
| (Adjusted to pH 8.0 with monoethanolamine) | |
| Total | 100.0 |

Laccase 14.0[3]: equivalent to ΔDO = 2.0

The above-mentioned components were uniformly mixed in the usual way to give a hair dye of treatment type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in red brown. This color was the same as that obtained when the hair dye was used immediately after production. In addition, this hair dye gave good hand to the treated hair and produced good treatment effect.

EXAMPLE 20

One-Pack Hair Dye (Treatment Type)

| Components | Amount (mass %) |
|---|---|
| 5,6-dihydroxyindoline hydrobromide | 1.0 |
| 5,6-dihydroxyindole hydrochloride | 1.0 |
| N-methyl-5,6-dihydroxyindoline hydrobromide | 0.5 |
| N-methyl-5,6-dihydroxyindole hydrochloride | 0.5 |
| 5-aminoindole hydrochloride | 0.25 |

-continued

| Components | Amount (mass %) |
|---|---|
| 2,3-dimethyl-5,6-dihydroxyindoline hydrobromide | 0.25 |
| Oleic acid | 0.5 |
| Linoleic acid | 0.5 |
| β-cyclodextrin | 2.0 |
| Laccase | 14.0[3] |
| N-acetyl-L-cysteine | 1.0 |
| Thiourea | 0.5 |
| Stearyl trimethylammonium chloride | 0.5 |
| Cetyl trimethylammonium chloride | 0.5 |
| Cetostearyl alcohol | 4.0 |
| Oleyl alcohol | 1.0 |
| Ethyl oleate | 0.5 |
| Isopropyl palmitate | 0.5 |
| Liquid paraffin | 1.0 |
| Beeswax | 0.5 |
| POE (40) hardened castor oil triisostearate | 0.25 |
| POE (20) hardened castor oil triisostearate | 0.25 |
| POE (30) stearyl ether | 0.75 |
| Sorbitan monostearate | 1.0 |
| Glycerin monostearate | 0.5 |
| Methylparaben | 0.3 |
| Propylene glycol | 5.0 |
| 1,3-butylene glycol | 3.0 |
| Lactic acid | 0.2 |
| Perfume | 0.1 |
| Purified water | balance |
| (Adjusted to pH 7.5 with monoethanolamine) | |
| Total | 100.0 |

Laccase 14.0[3]: equivalent to ΔDO = 2.0

The above-mentioned components were uniformly mixed in the usual way to give a hair dye of treatment type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in dark gray black. This color was the same as that obtained when the hair dye was used immediately after production. In addition, this hair dye gave good hand to the treated hair and produced good treatment effect.

EXAMPLE 21

One-Pack Hair Dye (Gel Type)

| Components | Amount (mass %) |
|---|---|
| p-phenylenediamine | 1.0 |
| 2,5-diaminotoluene sulfate | 2.0 |
| m-phenylenediamine | 0.5 |
| p-aminophenol | 0.5 |
| 2-(2'-hydroxyethylamino)-5-aminotoluene sulfate | 0.15 |
| Oleic acid | 0.2 |
| β-cyclodextrin | 1.0 |
| Laccase | 5.5[4] |
| Xanthan gum | 0.5 |
| N-acetyl-L-cysteine | 0.1 |
| Hydroxyethyl cellulose | 1.0 |
| POE (40) lauryl ether | 1.0 |
| POE (30) hardened castor oil | 1.0 |
| Ethanol | 10.0 |
| Glycolic acid | 0.2 |
| Perfume | 0.1 |
| Purified water | balance |
| (Adjusted to pH 6.5 with monoethanolamine) | |
| Total | 100.0 |

Laccase 5.5[4]: equivalent to ΔDO = 0.8

The above-mentioned components were uniformly mixed in the usual way to give a hair dye of gel type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in blue black. This color was the same as that obtained when the hair dye was used immediately after production.

EXAMPLE 22

One-Pack Hair Dye (Gel Type)

| Components | Amount (mass %) |
|---|---|
| 5,6-dihydroxyindoline hydrobromide | 1.0 |
| 5,6-dihydroxyindole hydrochloride | 1.0 |
| N-ethyl-5,6-dihydroxyindole hydrobromide | 0.05 |
| Oleic acid | 0.2 |
| β-cyclodextrin | 1.0 |
| Laccase | 5.5[4] |
| Xanthan gum | 0.5 |
| N-acetyl-L-cysteine | 1.0 |
| Hydroxyethyl cellulose | 1.0 |
| POE (40) lauryl ether | 1.0 |
| POE (30) hardened castor oil | 1.0 |
| Ethanol | 10.0 |
| Glycolic acid | 0.2 |
| Perfume | 0.1 |
| Purified water | balance |
| (Adjusted to pH 6.8 with monoethanolamine) | |
| Total | 100.0 |

Laccase 5.5[4]: equivalent to ΔDO = 0.8

The above-mentioned components were uniformly mixed in the usual way to give a hair dye of gel type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in black. This color was the same as that obtained when the hair dye was used immediately after production.

EXAMPLE 23

One-Pack Eyelash Dye (Gel Type)

| Components | Amount (mass %) |
|---|---|
| 2,5-diaminotoluene sulfate | 2.0 |
| Nitro-p-phenylenediamine | 1.5 |
| p-aminophenol | 0.5 |
| m-aminophenol | 0.3 |
| Sodium oleate | 0.2 |
| β-cyclodextrin | 1.0 |
| Laccase | 3.5[5] |
| N-acetyl-L-cysteine | 0.5 |
| Thiourea | 0.3 |
| Hydroxyethyl cellulose | 0.1 |
| $C_{10}$ polycarbamyl polyglycol ester | 0.1 |
| POE (40) lauryl ether | 1.0 |
| Ethanol | 10.0 |
| Glycolic acid | 0.2 |
| Perfume | 0.1 |
| Purified water | balance |
| (Adjusted to pH 8.0 with monoethanolamine) | |
| Total | 100.0 |

Laccase 3.5[5]: equivalent to ΔDO = 0.5

The above-mentioned components were uniformly mixed in the usual way to give an eyelash dye of gel type. After storage for six months at room temperature or for one month at 45° C., the above-mentioned eyelash dye was evaluated by ten female panelists. All the panelists had their eyelash dyed apparently in red. It was found that the eyelash dye kept its dyeing power even after storage. Thus this eyelash dye was rated as excellent.

EXAMPLE 24

One-Pack Eyebrow Dye (Soft Cream Type)

| Components | Amount (mass %) |
| --- | --- |
| 2,5-diaminotoluene sulfate | 2.0 |
| m-phenylenediamine | 2.5 |
| Oleic acid | 0.5 |
| Linoleic acid | 0.5 |
| β-cyclodextrin | 2.0 |
| Laccase | 10.5[6] |
| N-acetyl-L-cysteine | 0.5 |
| Thiourea | 0.3 |
| Cetostearyl alcohol | 2.5 |
| POE (3) lauryl ether sulfate | 0.8 |
| Oleyl alcohol | 1.0 |
| Alkyl acrylate · alkyl methacrylate · polyoxyethylene (20) stearyl ether copolymer | 1.0 |
| Isopropyl myristate | 0.5 |
| POE (40) glycerin isostearate | 0.25 |
| POE (20) glycerin isostearate | 0.25 |
| Sorbitan sesquioelate | 1.0 |
| Methylparaben | 0.3 |
| Propylene glycol | 5.0 |
| Glycolic acid | 0.2 |
| Perfume | 0.1 |
| Purified water | balance |
| (Adjusted to pH 7.5 with monoethanolamine) | |
| Total | 100.0 |

Laccase 10.5[6]: equivalent to ΔDO = 1.5

The above-mentioned components were uniformly mixed in the usual way to give an eyebrow dye of cream type. After storage for six months at room temperature or for one month at 45° C., the above-mentioned eyebrow dye was evaluated by ten female panelists. All the panelists had their eyebrow dyed apparently in blue. It was found that the eyebrow dye kept its dyeing power even after storage. Thus this eyebrow dye was rated as excellent.

EXAMPLE 25

One-Pack Hair Dye (Cream Type)

| Components | Amount (mass %) |
| --- | --- |
| 2,5-diaminotoluene sulfate | 1.0 |
| HC red No. 1 | 1.0 |
| HC red No. 16 | 0.5 |
| 4-amino-m-cresol | 0.2 |
| 1,3-bis-(2,4-diaminophenoxy)-propane | 0.5 |
| 4-chlororesorcinol | 0.15 |
| Linoleic acid | 0.2 |
| β-cyclodextrin | 1.0 |
| Laccase | 14.0[7] |
| N-acetyl-L-cysteine | 0.8 |
| Stearyl trimethylammonium chloride | 0.2 |
| Cetostearyl alcohol | 1.5 |
| POE (40) glycerin triisostearate | 0.75 |
| POE (20) lauryl ether | 0.5 |
| POE (30) oleyl ether | 0.5 |

-continued

| Components | Amount (mass %) |
| --- | --- |
| Sorbitan monostearate | 1.0 |
| Methylparaben | 0.3 |
| Propylene glycol | 5.0 |
| Lactic acid | 0.2 |
| Perfume | 0.1 |
| Purified water | balance |
| (Adjusted to pH 7.0 with monoethanolamine) | |
| Total | 100.0 |

Laccase[7]: equivalent to ΔDO = 2.0

The above-mentioned components were uniformly mixed in the usual way to give a hair dye of cream type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in pretty dark red. This color was the same as that obtained when the hair dye was used immediately after production.

EXAMPLE 26

One-Pack Hair Dye (Cream Type)

| Components | Amount (mass %) |
| --- | --- |
| 2,5-diaminotoluene sulfate | 1.0 |
| HC blue No. 2 | 1.0 |
| HC blue No. 7 | 0.5 |
| Hydroxyethyl-2-nitro-p-toluidine | 0.25 |
| 4-amino-2-hydroxytoluene | 0.15 |
| 1,5-naphthalenediol | 0.05 |
| 2-amino-3-hydroxypyridine | 0.05 |
| β-cyclodextrin | 1.0 |
| Laccase | 14.0[7] |
| N-acetyl-L-cysteine | 0.5 |
| Thiourea | 0.3 |
| Stearyl trimethylammonium chloride | 0.5 |
| Coconut oil fatty acid acyl-L-arginine ethyl-D,L-pyrrolidone carboxylate | 0.3 |
| Cetostearyl alcohol | 2.5 |
| Oleyl alcohol | 0.5 |
| POE (30) hardened castor oil | 0.75 |
| POE (30) cetyl ether | 0.75 |
| Sorbitan monostearate | 1.0 |
| Methylparaben | 0.3 |
| Propylene glycol | 2.0 |
| 1,3-butylene glycol | 2.0 |
| Glycolic acid | 0.2 |
| Perfume | 0.1 |
| Purified water | balance |
| (Adjusted to pH 7.5 with monoethanolamine) | |
| Total | 100.0 |

Laccase 14.0[7]: equivalent to ΔDO = 2.0

The above-mentioned components were uniformly mixed in the usual way to give a hair dye of cream type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in deep blue. This color was the same as that obtained when the hair dye was used immediately after production.

EXAMPLE 27

One-Pack Hair Dye (in the Form of Creamy Foam)

| Components (Stock solution) | Amount (mass %) |
|---|---|
| 2,5-diaminotoluene sulfate | 1.0 |
| HC yellow No. 6 | 0.7 |
| HC yellow No. 2 | 0.3 |
| HC orange No. 1 | 0.7 |
| 2-amino-6-chloro-4-nitrophenol | 0.3 |
| 2-amino-6-chloro-o-cresol | 0.3 |
| 2,6-dihydroxyethylaminotoluene | 0.1 |
| Hydroxyethyl-2-nitro-p-toluidine | 0.05 |
| Linoleic acid | 0.2 |
| β-cyclodextrin | 1.0 |
| Laccase | 10.5[8] |
| Sodium sulfite | 0.09 |
| N-acetyl-L-cysteine | 0.3 |
| Cetostearyl trimethylammonium chloride | 0.2 |
| Cetostearyl alcohol | 0.6 |
| POE (20) glycerin triisostearate | 0.2 |
| Sorbitan monostearate | 0.1 |
| POE (20) Oleyl ether | 0.2 |
| Methylparaben | 0.3 |
| Lactic acid | 0.2 |
| 1,3-butylene glycol | 5.0 |
| Perfume | 0.1 |
| Purified water | balance |
| (Adjusted to pH 7.0 with monoethanolamine) | |
| Total | 100.0 |

Laccase 10.5[8]: equivalent to ΔDO = 1.5

A stock solution was prepared in the usual way according to the above-mentioned formulation. The stock solution was placed in an aerosol can, which was subsequently clinched under vacuum. The aerosol can was filled with LPG (4.0 kg) as a propellant such that the ratio of stock solution to gas is 95:5 (by mass). Thus there was obtained a hair dye of aerosol type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in light golden color. This color was the same as that obtained when the hair dye was used immediately after production. In addition, when applied to European blond hair, this hair dye enhanced the blond color.

EXAMPLE 28

One-Pack Hair Dye (in the Form of Foam)

| Components (Stock solution) | Amount (mass %) |
|---|---|
| 2,5-diaminotoluene sulfate | 2.0 |
| 4-hydroxypropylamino-3-nitrophenol | 0.7 |
| N,N'-bis-(2-hydroxyethyl)-2-nitro-para-henylenediamine | 0.5 |
| 2,7-naphthalenediol | 0.3 |
| 2-methylresorcinol | 0.3 |
| Oleic acid | 0.2 |
| Oleyl alcohol | 0.2 |
| β-cyclodextrin | 1.0 |
| Laccase | 7.0[9] |
| Cationized hydroxyethyl cellulose | 0.5 |
| N-acetyl-L-cysteine | 1.0 |
| Sorbitan sesquioleate | 1.5 |
| Ethanol | 10.0 |
| Glycolic acid | 0.2 |
| Perfume | 0.1 |
| Purified water | balance |
| (Adjusted to pH 6.5 with monoethanolamine) | |
| Total | 100.0 |

Laccase 7.0[9]: equivalent to ΔDO = 1.0

A stock solution was prepared in the usual way according to the above-mentioned formulation. The stock solution was placed in an aerosol can, which was subsequently clinched under vacuum. The aerosol can was filled with LPG (2.0 kg) as a propellant such that the ratio of stock solution to gas is 95:5 (by mass). Thus there was obtained a hair dye of aerosol type. The LPG as a compressed gas may be replaced by any one or more of nitrogen, carbon dioxide gas, dinitrogen monoxide gas, flon 11, flon 12, and flon 114. The aerosol type may be direct spray type or piston type in an aluminum can or tinplate can, or the aerosol can may be double-walled can such as back-in type and EXXEL type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in blackish indigo blue. This color was the same as that obtained when the hair dye was used immediately after production.

EXAMPLE 29

One-Pack Hair Dye (in the Form of Foam)

| Components (Stock solution) | Amount (mass %) |
|---|---|
| 2,5-diaminotoluene sulfate | 2.0 |
| 4-amino-2-nitiodiphenylamine-2'-carboxylic acid | 1.0 |
| Tetrahydro-6-nitroquinoxaline | 1.0 |
| 2-aminomethyl-p-aminophenol hydrochloride | 0.5 |
| 2-amino-6-chloro-4-nitrophenol | 0.3 |
| 2,4-diaminophenoxyethanol hydrochloride | 0.3 |
| Linoleic acid | 0.2 |
| Oleyl alcohol | 0.2 |
| β-cyclodextrin | 1.0 |
| Laccase | 7.0[9] |
| Hydroxyethyl cellulose | 0.5 |
| Coconut oil fatty acid sodium acyl-glutamate | 1.0 |
| N-acetyl-L-cysteine | 0.5 |
| Thiourea | 0.3 |
| Sodium polyacrylate (cross-linked type) | 2.5 |
| Ethanol | 10.0 |
| Propylene glycol | 5.0 |
| Lactic acid | 0.2 |
| Perfume | 0.1 |
| Purified water | balance |
| (Adjusted to pH 6.8 with monoethanolamine) | |
| Total | 100.0 |

Laccase 7.0[9]: equivalent to αDO = 1.0

A stock solution was prepared in the usual way according to the above-mentioned formulation. The stock solution was placed in an aerosol can, which was subsequently clinched under vacuum. The aerosol can was filled with LPG (2.0 kg) as a propellant such that the ratio of stock solution to gas is 95:5 (by mass). Thus there was obtained a hair dye of aerosol type. After storage for six months at room temperature or for one month at 45° C., the above-mentioned hair dye was applied in an adequate amount to 1.0 g of white hair, and after standing for 20 minutes, the hair was washed with water and shampooed. The treated hair was dried by a drier. It was found that the hair was dyed in dark brown. This color was the same as that obtained when the hair dye was used immediately after production.

EXAMPLE 30

One-Pack Hair Dye (in the Form of Creamy Foam)

| Components (Stock solution) | Amount (mass %) |
| --- | --- |
| 2,5-diaminetoluene sulfate | 2.0 |
| 2-amino-3-hydroxypyridine | 1.0 |
| 2,6-dihydroxyethylaminotoluene | 0.5 |
| 4-amino-3-nitrophenol | 0.3 |
| 2,6-dihydroxy-3,4-dimethylpyridine | 0.3 |
| Oleic acid | 0.2 |
| β-cyclodextrin | 1.2 |
| Laccase | 10.5[10] |
| Xanthan gum | 0.05 |
| Sodium sulfite | 0.05 |
| Thiourea | 0.05 |
| N-acetyl-L-cysteine | 0.2 |
| Stearyl trimethylammonium chloride | 0.2 |
| Cetostearyl alcohol | 1.0 |
| N-lauroyl-N-methyl-β-alanine triethanolamine | 0.5 |
| POE (20) glycerin triisostearate | 0.2 |
| Sorbitan monooleate | 0.2 |
| Methylparaben | 0.3 |
| Glycolic acid | 0.2 |
| Propylene glycol | 15.0 |
| Perfume | 0.1 |
| Purified water | balance |
| (Adjusted to pH 7.0 with monoethanolamine) | |
| Total | 100.0 |

Laccase 10.5[10]: equivalent to ΔDO = 1.5

A stock solution was prepared in the usual way according to the above-mentioned formulation. The stock solution was placed in an aerosol can, which was subsequently clinched under vacuum. The aerosol can was filled with LPG (4.0 kg) as a propellant such that the ratio of stock solution to gas is 95:5 (by mass). Thus there was obtained a creamy hair dye of aerosol type. After storage for six months at room temperature or for one month at 45° C., the above-mentioned hair dye was applied (in an adequate amount) to 1.0 g of white hair, and after standing for 20 minutes, the hair was washed with water and shampooed. The treated hair was dried by a drier. It was found that the hair was dyed in dark brown. This color was the same as that obtained when the hair dye was used immediately after production.

The composition for dyeing keratinous fiber according to the present invention is incorporated with a weak reducing agent as mentioned above, so that it is available in one-pack form (in place of a mixed type which needs the mixing of two packs before use) for consumer's convenience. Even though it is of one-pack type, it remains stable without aggregates, precipitates, and discoloration during storage at high temperatures. Its stability is enhanced by incorporation with cyclodextrin. It produces its effect through reaction between oxidase and oxidative color-developing substance regardless of its form (aerosol, cream, gel, and liquid).

What is claimed is:

1. A one-pack type composition for dyeing keratinous fiber which comprises incorporated therein an oxidative color-developing substance, an enzyme which reacts with oxygen as a substrate but does not evolve hydrogen peroxide, and a weak reducing agent, and cyclodextrin.

2. A The composition for dyeing keratinous fiber of claim 1, where said oxidative color-developing substance is selected from the group consisting of p-phenylenediamine, a salt of p-phenylenediamine, toluene-2,5-diamine, a salt of toluene-2,5-diamine, p-aminophenol, 5-amino-o-cresol, p-methylaminophenol, 5-amino-o-cresol, p-methylaminophenol sulfate, m-aminophenol, p-nitro-o-phenylenediamine, 2,6-diaminopyridine, resorcinol, o-aminophenol and m-phenylenediamine.

3. The composition for dyeing keratinous fiber of claim 1, further comprising a coupler.

4. The composition for dyeing keratinous fiber of claim 1, further comprising a cationic direct dye.

5. The composition for dyeing keratinous fiber of claim 1, wherein said enzyme which reacts with oxygen as a substrate but does not evolve hydrogen peroxide is selected from the group consisting of catechol oxidase, laccase and a combination thereof.

6. The composition for dyeing keratinous fiber of claim 1, wherein said enzyme which reacts with oxygen as a substrate but does not evolve hydrogen peroxide is in the amount of 0.01 to 50% of the total amount of the composition.

7. The composition for dyeing keratinous fiber of claim 1, wherein said enzyme which reacts with oxygen as a substrate but does not evolve hydrogen peroxide is in the amount of 0.1 to 30% of the total amount of the composition.

8. The composition for dyeing keratinous fiber of claim 1, wherein said weak reducing agent has a pseudo first-order reaction rate constant $K_{obs}$ (as an index of reducing capacity) that is smaller than $0.001\ s^{-1}$.

9. The composition for dyeing keratinous fiber of claim 1, wherein said weak reducing agent is selected from the group consisting of sodium thiosulfate, dl-cysteine, N-acetyl-L-cysteine, thiourea, dithioglycolic acid, L-ascorbic acid, sorbic acid, adipic acid and salts thereof.

10. The composition for dyeing keratinous fiber of claim 1, wherein the amount of said cyclodextrin is 0.1 to 75%.

11. The composition for dyeing keratinous fiber of claim 1, wherein the amount of said cyclodextrin is 0.5 to 60%.

12. The composition for dyeing keratinous fiber of claim 1, further comprising an ingredient selected from the group consisting of a pH adjustor, surface active agent, ionic or nonionic natural or synthetic or semisynthetic polymeric compound, ester oil, vegetable oil, silicon derivative, fluorine derivative, amino acid, salts, alcohol, dandruff remover, chelating agent, preservatives, UV absorber, fungicide, antioxidant, perfume, acid dye and natural dye.

* * * * *